United States Patent [19]

Kaplan et al.

[11] 4,026,888

[45] May 31, 1977

[54] CERTAIN DERIVATIVES OF PARTICULAR 3-THIOLATED CEPHALOSPORINS

[75] Inventors: Murray A. Kaplan, Syracuse; William J. Gottstein, Fayetteville; Alphonse P. Granatek, Baldwinsville, all of N.Y.

[73] Assignee: Bristol-Myers Company, New York, N.Y.

[22] Filed: Jan. 30, 1976

[21] Appl. No.: 653,999

Related U.S. Application Data

[63] Continuation-in-part of Ser. No. 622,306, Oct. 10, 1975, abandoned.

[52] U.S. Cl. ............................ 260/243 C; 424/246
[51] Int. Cl.² ........................................ C07D 501/20
[58] Field of Search ............................. 260/243 C

[56] References Cited

UNITED STATES PATENTS

| | | | |
|---|---|---|---|
| 3,647,781 | 3/1972 | Wieslogle et al. | 260/243 C |
| 3,855,213 | 12/1974 | Dunn et al. | 260/243 C |
| 3,867,380 | 2/1975 | Dunn et al. | 260/243 C |
| 3,899,394 | 8/1975 | Willner et al. | 260/243 C |

*Primary Examiner*—Nicholas S. Rizzo
*Attorney, Agent, or Firm*—Herbert W. Taylor, Jr.

[57] ABSTRACT

Compounds of the formula

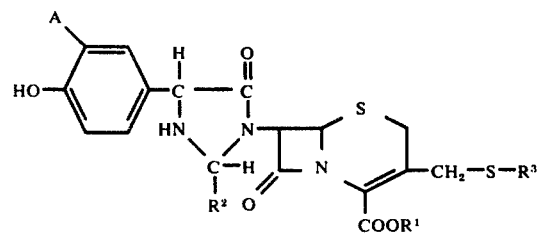

wherein
A is hydrogen, hydroxy, methyl or methoxy,
$R^1$ is hydrogen, sodium or potassium,
$R^2$ is carboxyl or an aliphatic, aromatic or heterocyclic radical to which there is also attached a strongly acidic group in the form of its sodium or potassium salt, and
$R^3$ is 1,2,3-triazol-5-yl, such group being unsubstituted or substituted with one or two lower alkyl groups of one to four carbon atoms are prepared by reacting the appropriate aldehyde with the corresponding amphoteric cephalosporin. A preferred product has the structure

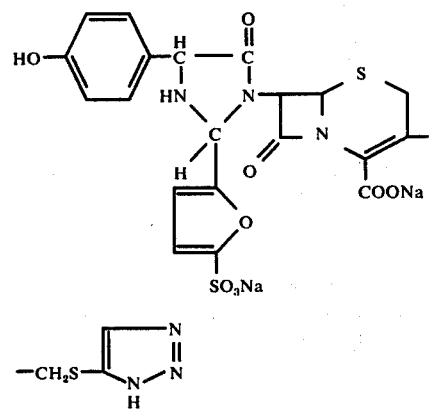

59 Claims, No Drawings

CERTAIN DERIVATIVES OF PARTICULAR 3-THIOLATED CEPHALOSPORINS

CROSS-REFERENCE TO RELATED APPLICATIONS

This application is a continuation-in-part of our prior, copending application Ser. No. 622,306 filed Oct. 10, 1975, and now abandoned.

BACKGROUND OF THE INVENTION

1. Field of the Invention

The cephalosporin derivatives of the present invention possess in general the usual attributes of that family of antibacterial agents and are particularly useful in the treatment of bacterial infections.

2. Description of the prior art

Derivatives of various α-amino cephaosporins with nitrosubstituted heterocyclic aldehydes are described in U.S. Pat. No. 3,647,781. Reaction products of various α-amino cephalosporins with formaldehyde are disclosed in South African Pat. No. 72/8475, with acetaldehyde in South African Pat. No. 72/8474 and with various aldehydes and ketones in South African Pat. No. 72/8476.

Derivatives of cephalosporins having in the acylamido group at the 7-position an α-amino group which has been reacted with an aldehyde (but limited to methyl or acetoxymethyl at the 3-position) are disclosed in U.S. Pat. No. 3,880,842; U.S. Pat. No. 3,887,546 and Farmdoc 49804W.

For a few examples of the starting materials used to make the compounds of the present invention see U.S. Pat. No. 3,899,394; U.S. Pat. No. 3,855,213; U.S. Pat. No. 3,867,380; Farmdoc 38983T; Farmdoc 57268V; Farmdoc 49048 V and Farmdoc 49692W.

SUMMARY OF THE INVENTION

At its broadest the present invention provides the condensation products of aldehydes other than formaldehyde and acetaldehyde with 3-(1,2,3-triazol-5-ylthiomethyl)cephalosporins as a "3-thiolated-cephalosporin" having at the 7-position an α-aminophenylacetamido substituent which can be unsubstituted in the benzene ring or substituted with one, two or three groups which are unreactive toward aldehydes and preferably with a para-hydroxy or a para-acetoxy group. By "3-thiolated-cephalosporin" is meant a derivative of cephalosporanic acid in which the acetoxy group has been displaced by a thiol to covert the 3-acetoxymethyl group to a 3-(substituted)-thiomethyl group; preferred thiols are those n which the mercapto group is attached to a carbon atom in a 5-membered heterocyclic ring containing three atoms, said ring being optionally substituted with one or two alkyl or alkoxy groups containing 1 to 4 carbon atoms, methylthio or trifluoromethyl.

The resulting condensation products in the form of their sodium and potassium salts exhibit desirable solubility, stability and absorption. The preferred species hydrolyze rapidly and completely in the body to regenerate the original amphoteric 3-thiolated cephalosporin; this is not the case with corresponding condensation products with acetaldehyde, formaldehyde or acetone which hydrolyze completely but at an undesirably slower rate.

There is thus provided the sodium or potassium salt of the equimolar condensation product of a) an aldehyde other than formaldehyde or acetaldehyde with b) an amphoteric 3-thiolated cephalosporin containing an α-substituted-α-aminoacetamido group at the 7-position and having in its zwitterion form an aqueous solubility of less than 125 mgm./ml. and in a preferred embodiment there is provided the sodium or potassium salt of the equimolar condensation product of a) an aldehyde having the formula $R^2$-CHO wherein $R^2$ is carboxyl or an aliphatic, aromatic or heterocyclic radical to which there is also attached a strongly acidic group in the form of its sodium or potassium salt with b) an amphoteric 3-thiolated cephalosporin containing an α-substituted-α-aminocetamido group at the 7-position and having in its zwitterion form an aqueous solubility of less than 125 mgm./ml.; in a narrower preferred embodiment the aldehyde bearing the acidic group is 5-formyl-2-furansulfonic acid, o-benzaldehyde sulfonic acid, 4-methoxybenzaldehyde-3-sulfonic acid, 4-hydroxybenzaldehyde-3-sulfonic acid, o- and p-formylphenoxyacetic acid, 5-formyl-salicylic acid, p-formyl-cinnamic acid, glyoxalic acid, phthalaldehydic acid, p-formyl-benzoic acid, acetaldehyde sulfonic acid sodium salt or acetaldehyde disulfonic acid sodium salt.

The present invention provides the compounds of the formula

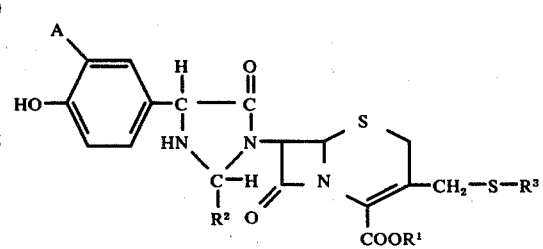

wherein

A is hydrogen, hydroxy, methyl or methoxy, $R^1$ is hydrogen, sodium or potassium, $R^2$ is carboxyl or an aliphatic, aromatic or heterocyclic radical to which there is also attached a strongly acidic group in the form of its sodium or potassium salt, and $R^3$ is 1,2,3-triazol-5-yl, such group being unsubstituted or substituted with one or two lower alkyl groups of one to four carbon atoms. In the preferred embodiments the carbon atom attached to the benzene ring (para to the hydroxyl group) has the D configuration.

The present invention thus provides watersoluble, pharmaceutically acceptable derivatives of the amphoteric cephaloporins having the structure

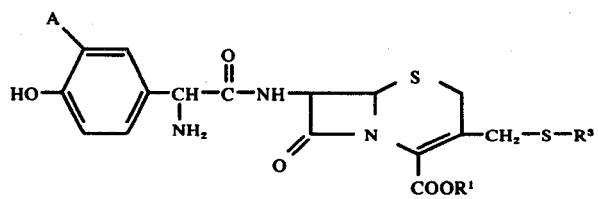

wherein A, $R^1$ and $R^3$ have the meaning set forth above. In the preferred embodiment the carbon bearing the α-amino group has the D configuration. These are derivatives which (1) upon the addition of water will give true solutions for parenteral administration, (2) have acceptable thermal stability in the solid state, (3) in aqueous solution have a useful life of a least several hours at room temperature and (4) on intravenous or intramuscular injection result in little or no muscle or vein irritation. More particularly, the present invention provides alkali metal salts, especially sodium and potassium salts, of the reaction products of said amphoteric cephalosporins with aldehydes and preferably with an aldehyde containing an acidic group, e.g. 2-furansulfonic acid.

The compounds of the present invention exhibit desirable solubility, stability and absorption. The preferred species hydrolyze rapidly and completely in the body to regenerate the original amphoteric cephalosporin of formula II; this is not the case with corresponding derivatives made from fromaldehyde, acetaldehyde or acetone which hydrolyze completely but at an undesirably slower rate. The compounds of the present invention thus overcome the problems posed by the instability to high pH and frequent relative insolubility in thier zwitterion form of the amphoteric cephlosporins of formula II; the problems include rapid inactivation and relatively poor absorption upon oral and parenteral administration.

In the preferred embodiments of the present invention the aldehyde with an acidic function is selected from the group consisting of

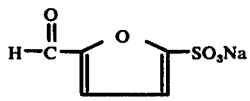

5-formyl-2-furansulfonic acid sodium salt,

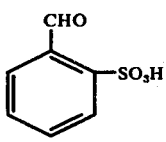

o-benzaldehyde sulfonic acid,

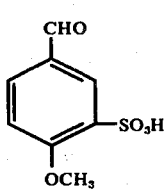

4-methoxybenzaldehyde-3-sulfonic acid,

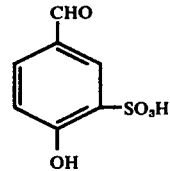

4-hydroxybenzaldehyde-3-sulfonic acid,

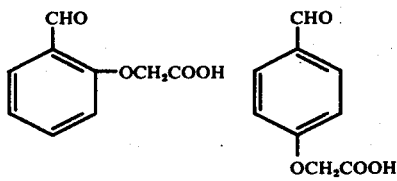

o- and p-formylphenoxyacetic acid,

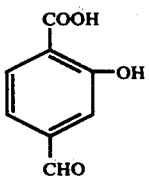

5-formyl-salicylic acid,

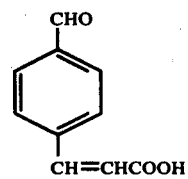

p-formyl-cinnamic acid,

OCH — COOH glyoxalic acid,

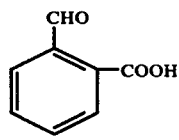

phthalaldehydic acid,

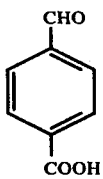

p-formyl-benzoic acid,

acetaldehyde sulfonic acid sodium salt and

acetaldehyde disulfonic acid sodium salt.

Further preferred embodiments of the present invention are those of formula I wherein A is hydrogen, $R^2$ is derived from one of the aldehydes named above and most preferably is

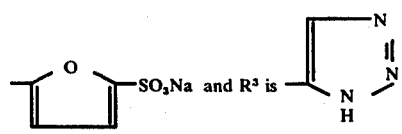

The compounds of the present invention solve the problem of formulating relatively water-insoluble (less than 125 mgm./ml.) amphoteric 3-thiolated cephalosporins for intravenous injection which requires true solutions having a concentration of about 250 mgm. in only one or two milliliters for bolus injection. In addition, such a dosage form can be distributed as a dry-fill (bottle of powder only) which is reconstituted just before use by the addition of sterile water but at that time it must also dissolve completely in a matter of a few minutes to be practical for such use.

In addition, when added (after such reconstitution) to a larger volume of infusion fluid for intravenous drip to give a concentration in the range of 10–25 mgm./ml., the compound must not lose more than 10% of its bioactivity over the 4–6 hours required for the infusion.

Amphoteric 3-thiolated cephalosporins having in their zwitterion form an aqueous solubility of less than about 125 mgm./ml. are clearly not suitable and in addition (unlike their non-amphoteric counterparts such as cephalothin etc.) usually cannot be converted to ordinary, soluble sodium salts because the pH required is so high it causes decomposition and in addition the free amino group existing at that pH is thought to catalyze decomposition.

There is also provided by the present invention a process for the preparation of a compound of the formula

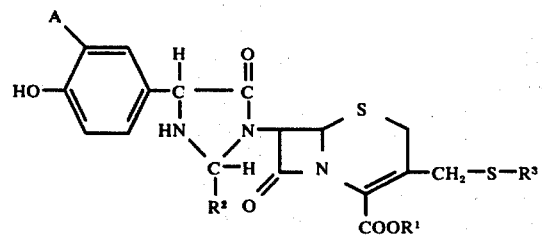

wherein
A is hydrogen, hydroxy, methyl or methoxy,
$R^1$ is hydrogen, sodium or potassium,
$R^2$ is carboxyl or an aliphatic, aromatic or heterocyclic radical to which there is also attached a strongly acidic group in the form of its sodium or potassium salt, and
$R^3$ is 1,2,3-triazol-5-yl, such group being unsubstituted or substituted withone or two lower alkyl groups of one to four carbon atoms which comprises 1. treating an aqueous suspension of an amphoteric cephalosporin of formula II or a solvate or hydrate thereof with an aldehyde having the formula $R^2CHO$ wherein $R^2$ is as defined above and sufficient water-soluble sodium or potassium base to raise the pH of the reaction mixture to between about 5.5 and 7.2 and to form in solution the desired compound I; and
2. recovering from that solution said compound.

The compounds of formula I have an asymmetric center at the carbon attached to two nitrogen atoms. Thus, compounds of formula I may exist in the form of the DL mixture or as the individual D or L isomers.

The starting material cephalosporin used in Step (1) of the above process may be any form of the amphoteric cehalosporin of formula II including the free acid zwitterion or a hydrate or solvate of said zwitterion.

The concentration of amphoteric cehalosporin starting material is not critical, and good results have been obtained with concentrations between about 24–300 milligrams cephalosporin tarting material per milliliter of solvent. The starting material is preferably ground and screened to a finely divided state, most preferably ground to a particle size of less than 200 mesh, so as to increase the surface area and rate of reaction.

The amphoteric cephalosporin starting material is slurried in water to form an aqueous suspension. An alternative to using n aqueous suspension in Step (1) would be to suspend the cephalosporin starting material in a organic solvent which is (1) a solvent for the alkali metal salt end-product, (2) miscible with the aldehyde, (3) chemically inert toward the cephalosporin starting material and end-product and (4) easily removable from the end-product as by mild drying. Examples of organic solvents which might be employed are dimethylsulfoxide and dimethylformamide. Because of the difficulty of removing residual organic solvent from the alkali metal salt end-product, however, the starting material is preferably provided as an aqueous suspension.

After obtaining the cephalosporin starting material in suspension, the desired alkali metal salt of formula I is formed in solution by addition of the aldehyde and an amount of water-soluble alkali metal base, preferably a sodium or potassium base, sufficient to raise the pH of the reaction mixture to between about 5.5 and 8. As the pH is raised to within this range the alkali metal salt of the reaction product of the amphoteric cephalosporin and the aldehyde is formed and goes into solution.

The temperature at which Step (1) is carried out is not critical. The reaction can be performed at room temperature; but higher or lower temperatures may be used and temperatures in the range of 50°–60° C. are preferred if the pH is between 5.5 and 6.8.

About 1 mole of the aldehyde is needed per mole of cephalosporin starting material but the aldehyde is preferably added somewhat in excess of the theoretical amount needed so as to ensure complete reaction, i.e. a slight molar excess. The most preferred ratio of aldehyde to cephalosporin starting material is about 1:1.

The alkali metal base may be any water soluble base capable of (1) providing alkali metal cations, preferably sodium or potassium ions, and (2) raising the pH of the reaction mixture to between about 5.5 and 8, most preferably about 6.2 to 7.2. Preferred bases because of their desirable solubility properties are sodium or potassium hydroxide. The $R^3$-S- moiety of compound I may split off at high pH. For this reason the base is added to the reaction mixture in such a manner that the pH is not allowed to rise above about 8. Preferably the base is used in the form of an aqueous solution and is added slowly to the reaction mixture with stirring until the reaction is shown to be complete by pH measurement and by formation of a solution or near solution. The amount of base used is not critical, but preferably about 1 mole of base is used per mole of cephalosporin starting material.

For best results the solution obtained at the conclusion of Step (1) is filtered to remove solid impurities prior to the recovery Step (2). Before filtration, the solution may optionally be carbon-treated with activated carbon to assist in removal of any colored impurities.

The desired product of formula I is then recovered from aqueous or non-aqueous solution as by precipitation or lyophilization. Precipitation of the alkali metal salt may be effected by addition of an organic solvent in which the desired salt is insoluble, i.e. an antisolvent. Examples of such antisolvents include isopropanol, n-propanol, t-butanol and acetonitrile.

The solvent to be used in the precipitation step should be one which can be easily removed from the end-product under conditions which will not result in any significant decomposition of the alkali metal salt. The most preferred antisolvent is isopropanol. The antisolvent may be added to the solution resulting from Step (1) or, alternatively and preferably, the solution containing the desired alkali metal salt is added with stirring to a large excess of the antisolvent. The alkali metal salt of formula I is then recovered by filtration, washed with a suitable organic solvent, e.g. isopropanol, and dried by conventional procedures, e.g. vacuum-drying at 50°–56° C. for 24–48 hours or air drying at 60° C. for 48 hours. As an alternative procedure to recovering the end-product by precipitation, the salt of formula I may also be recovered by lyophilization of the solution prepared in Step (1).

An alternative process for preparing the compounds of formula I comprises 1. forming a suspension of the amphoteric cephalosporin or a solvate or hydrate thereof in a suitable inert organic solvent, said solvent being a solvent for the triethylamine salt of the aldehyde reaction product of the amphoteric cephalosporin and a non-solvent for the alkali metal salt of formula I;

2. treating the suspension with the aldehyde and sufficient triethylamine to form in solution the triethylamine salt of the aldehyde reaction product of the amphoteric cephalosporin; and 3. precipitating the desired alkali metal salt of formula I from the solution by adding a solvent-soluble sodium or potassium base.

The starting material is slurried in an inert organic solvent which is a solvent for the triethylamine salt of the aldehyde reaction product of the amphoteric cephalosporin but which is an non-solvent for the desired alkali metal salt of formula I. The solvent selected for Step (1) should preferably be easily removable from the end-product under conditions which will not result in any appreciable decomposition of the end-product. Appropriate solvents for Step (1) may be determined by simple test.

The suspension formed in Step (1) is then treated with an aldehyde, preferably with a molar excess and most preferably with from about 1.3 to 1.4 moles of the aldehyde per mole of cephalosporin starting material, and sufficient triethylamine to form in solution the triethylamine salt of the cyclic reaction product of the aldehyde and the amphoteric cephalosporin. The reaction mixture is preferably stirred for at least about 30 minutes to ensure complete reaction. The amount of triethylamine used is not critical but preferably about 1 mole is used per mole of cephalosporin starting material. The reaction of Step (2) is conveniently done at room temperature but temperatures higher or lower than this may be selected with the expected decrease or increase, respectively, in reaction time.

After formation of a solution or near-solution in Step (2), the reaction mixture is preferably carbon-treated and filtered as in the first-mentioned process discussed above.

The desired alkali metal salt of formula I may then be recovered from the solution of Step (2) by addition of a solvent-soluble sodium or potassium salt. The preferred salts are sodium or potassium salts of organic acids having between about 2 and 18 carbon atoms, e.g. solvent-soluble salts of such acids as 2-ethylhexanoic, caproic, oleic, glycolic, propionic, acetic, etc. Preferred salts for the methanol solvent system are sodium or potassium 2-ethylhexanoate, most preferably solutions of these salts in a methanolmiscible organic solvent such as isopropanol. The most preferred alkali metal salts are solutions of sodium or potassium 2-ethylhexanoate in isopropanol. The alkali metal salt is added, preferably slowly and with stirring, in sufficient quantity so as to obtain the maximum amount of precipitate from the solution. After complete precipitation has been effected, the reaction mixture is stirred, preferably for at least about 1 hour, and then filtered. The precipitate is washed with an appropriate organic solvent, e.g. methanol, and dried by conventional procedures, e.g. vacuum-drying at 50° –56° C. for 24–48 hours or air drying at 60° C. for 48 hours.

The second process may also be carried out without use of the triethylamine in Step (2). In this modified procedure the suspension of the amphoteric cephalosporin or a solvate or hydrate thereof, preferably the methanol or propylene glycol solvate or sesquihydrate and most preferably the methanol solvate, is suspended in an inert organic solvent which is a non-solvent for the product of formula I, preferably methanol, and the suspension then treated with the aldehyde, preferably a molar excess, and a solvent-soluble sodium or potassium base, said base being added in an amount sufficient to raise the pH of the reaction mixture to between about 5.5 and 8. It is preferred to use as bases the sodium or potassium salts mentioned above as being preferred in the second process. In the modified process the cephalosporin starting material goes into solution and the insoluble alkali metal salt then precipitates out almost instantaneously. Since a solution is not obtained upon completion of the reaction, the reaction mixture is preferably stirred and heated to about 45° –50° C. for a period of time of up to several hours to ensure maximum yields of end-product. The solid product is removed by filtration, washed and dried to give the desired salt of formula I.

The alkali metal salts of the present invention may be used to provide pharmaceutical formulations of the amphoteric cephalosporin which have acceptable thermal stability in the solid state, high solubility in water, satisfactory aqueous stability, little or no muscle or vein irritation upon intravenous or intramuscular injection and excellent in vivo and in vitro antibacterial activity against a variety of Gram-positive and Gram-negative bacteria.

The sodium and potassium salts of formula I may be dissolved in water to form relatively concentrated solutions of at least 250 mg./ml. of activity. Concentrations of 250 mg./gl. of activity (pH 5.7-6.8) of these salts have acceptable aqueous stabilities.

In dilute aqueous solution the compounds of the present invention rapidly hydrolyze to the parent amphoteric cephalosporin of formula I. In acidic aqueous solutions at any concentration the compounds of this invention hydrolyze rapidly to said parent cephalosporin. This property makes them useful for purposes of purification of the parent amphoteric antibiotic, e.g. in solid form they can be washed with non-aqueous solvents to remove impurities soluble in such solvents and after such treatment are easily reconverted to the parent amphoteric antibiotic.

Activities of the compounds of formula I are substantially equivalent to those of the parent amphoteric cephalosporin.

In another aspect the present invention provides a pharmaceutical composition suitable upon reconstitution with water for use as a parenterally-administratable antibiotic formulation, said composition comprising a compound of formula I and a solid pharmaceutically acceptable water-soluble organic acid, said organic acid being present in an amount such that the pH of the formulation upon reconstitution with water is between about 5.5 and 7.5.

The dry mixture of salt of formula I and organic acid in the above-mentioned composition may be reconstituted with water to provide a high concentration, i.e. up to at least 250 mg./ml., solution suitable for parenteral administration. The composition provided by the present invention may also be prepared by admixing a compound of formula I with a sufficient amount of a pharmaceutically acceptable water-soluble solid organic acid such that the pH of the composition upon reconstitution with water is between about 5 and 7.

The organic acid used in the composition may be any non-toxic, water-soluble, solid organic acid. Examples of suitable acids include citric, tartaric, glycine hydrochloride, ascorbic, succinic, and the like. The most preferred acid for use in the composition of the present invention is citric acid.

The exact proportions of compound of formula I and solid organic acid are dependent on the physical and chemical properties of the acid selected, e.g. acidity, solubility, etc. Generally it is found that the desired pH range of 5-6 upon reconstitution with water is achieved when the solid organic acid is used in an amount of about 4-6% of the weight of the compound of formula I.

The compounds of formula I as well as the above-mentioned compositions are potent antibacterial agents useful by both oral and parenteral administration in the treatment of infectious diseases in poultry and animals, including man, caused by many Gram-positive and Gram-negative bacteria. The compounds ad compositions are also of value as nutritional supplements in animal feeds and as agents for the treatment of mastitis in cattle.

The salts and salt-organic acid mixtures of the present invention may be formulated as pharmaceutical compositions containing in addition to the active ingredient a pharmaceutically acceptable carrier or diluent.

The compounds may be administered either orally or parenterally, but because of their high solubility in water, are especially useful for parenteral administration. In the treatment of bacterial infections in man, the compounds and compositions may be administered in an amount of from about 5 to 20 mg./kg./day in divided dosage, e.g. 3 or 4 times a day. They are administered in dosage units containing, e.g. 125, 250 or 500 mg. of active ingredient.

Preparation of Starting Materials

Preparation of
7-[D-α-amino-α-(p-hydroxyphenyl)acetamindo]-3-(1,2,3-triazol-5-ylthiomethyl)-3-cephem-4-carboxylic acid methanol solvate In a three necked flask equipped with a reflux condenser, overhead stirrer and thermometer, there was placed a well mixed mixture of 8.36 g. (0.05 mole) of D-(-)-p-hydroxyphenylglycine and 3.02 g. (0.075 mole) of magnesium oxide in 120 ml. of 50% aqueous dioxane. The mixture was stirred for 1 hour and then treated with 10.74 g. (0.075 mole) of t-butoxycarbonylazide. The mixture was then stirred and heated at 45°-50° for 17 hours under $N_2$. The solution was diluted with 400 ml. of $H_2O$ and extracted twice with 300 ml. of ethyl acetate. The aqueous phase was acidified with 10% citric acid solution to pH 4 and saturated with NaCl. The aqueous mixture was extracted with 3 × 400 ml. of ethyl acetate. The solution was dried over $Na_2SO_4$ and the solvent evaporated. The residue was triturated with "Skellysolve B" to yield D-α-t-butoxycarbonylamino-α-(p-hydroxyphenyl)acetic acid as a solid weighing 10.4 g. (78.5%).

To a suspension of 7-amino-3-(1,2,3-triazol-5-ylthiomethyl)-3-cephem-4-carboxylic acid (6.0 g., 19.0 mmole) in 100 ml. dry methylene chloride there was added 8.5 ml. of 1,1,1,3,3,3-hexamethyldisilazane (40.9 mmole). The mixture was stirred and heated at reflux for 4 hours at which time a clear solution was obtained. The solvent was evaporated and the residual oil was subjected to high-vacuum overnight at room temperature. The foamy residue was dissolved in 85 ml. of dry THF (tetrahydrofuran) and cooled to about −15° before introduction into the subsequent reaction mixture.

D-α-t-Butoxycarbonylamino-α-(4-hydroxyphenyl)acetic acid, (4.4 g., 16.5 mmole) was dissolved in 145 ml. dry THF. The solution was stirred and cooled to −20°.

N-methylmorpholine (1.6 g., 16 mmoles) and isobutylchloroformate (2.3 g., 16.8 mmole) were added in succession at such rate that the temperature of the mixture did not rise about −10°. The resulting mixture was then stirred for 20 minutes at −12° to −15°. It was then cooled to −20° and the THF solution of silylated 7-amino-3-(1,2,3-triazol-5-ylthiomethyl)-3-cephem-4-carboxylic acid was added all at once. The temperature rose to about −12°. External cooling was discontinued until the temperature rose to 0°. At this point an ice-water bath was applied and the mixture stirred for 3 hours at 2°-3°. This was followed by a period of one hour without external cooling, the temperature rising to 20°. A total of 30 ml. methanol was added and the stirring continued for 15 minutes at room temperature. After evaporating the solvents under reduced pressure, the residue was suspended in 300 ml. ethyl acetate. The suspended solid was filtered off, (11.8 g.). The ethyl acetate solution was extracted three times with NaHCO$_3$ (5%) solution. The combined sodium bicarbonate extracts were cooled in an ice-bath, layered with ethyl acetate and acidified to a pH of 2.5 with 42.5% H$_3$PO$_4$. The phases were shaken and then separated. The ethyl acetate solution was then dried by passing it through sodium sulfate and then evaporated to about 15-20 ml. This solution was then added dropwise to stirred cyclohexane (~400 ml.) contained in an Erlenmeyer flask. After stirring for 1/2 hour the precipitated solid was collected by filtration. The collected, solid 7-[D-α-t-butoxycarbonylamino-α-(p-hydroxyphenyl)acetamido]-3-(-1,2,3-triazol-5-ylthiomethyl)-3-cephem-4-carboxylic acid was air dried. It weighed 1.75 g.

7-[D-α-t-Butoxycarbonylamino-α-(p-hydroxyphenyl)-acetamido]-3-(1,2,3-triazol-5-ylthiomethyl)-3-cephem-4-carboxylic acid, 3.5 g., was dissolved in Lb 80 ml. HCOOH, 98-100%, and stirred for 2 hours at room temperature. The HCOOH was evaporated under reduced pressure (aspirator bath temperature not above 40°) and finally azeotroped 3 times with 30 ml. of toluene. The solid was dried overnight under high vacuum over P$_2$O$_5$. A total of 3.5 g. of foam was obtained. The foam, 2 g., was stirred with 300 ml. of H$_2$O: CH$_3$OH (8:2). The solvent was filtered from some solid (0.3 g.), charcoaled with 700 mg. of "Darko KB", filtered through diatomaceous earth ("Celite") and freeze-dried to yield 0.9 g. of crude 7-[D-α-amino-α-(p-hydroxyphenyl)acetamido]-3-(1,2,3-triazol-5-ylthiomethyl)-3-cephem-4-carboxylic acid. To crystallize the following procedure was used. A suspension of 0.2 g. of the crude material in 6 ml. of 99% methanol was heated in a test tube to boiling. Immediately the heating was discontinued and the melt triturated with seeds. The melt solidified to a crystalline mass. In this manner a total of 0.211 g. of 7-[D-α-amino-α-(p-hydroxyphenyl)acetamido]-3-(1,2,3-triazol-5-ylthiometyl)-3-cephem-4-carboxylic acid was obtained from 0.400 g. of crude material. The material was dried at 56°/0.1 mm over P$_2$O$_5$ for 20 hrs., m.p. < 200° dec. IR and NMR are consistent with structure. The NMR indicated the presence of 1/3 mole of CH$_3$OH. Anal. Calcd. for C$_{18}$H$_{18}$N$_6$O$_5$S$_2$·H$_2$O·1/3CH$_3$OH: C, 44.83; H, 4.38; N, 17.10; S, 13.09. Found: C, 43.97; H, 4.36; N, 15.84; S, 6.18.

A total 6.5 g. (11.55 mmole) of 7-[D-α-t-butoxycarbonylamino-α-(p-hydroxyphenyl)acetamido]-3-(1,2,3-triazol-5-ylthiomethyl)-3-cephem-4-carboxylic acid was dissolved in 175 ml. 98-100% formic acid under anhydrous conditions. The mixture was stirred at room temperature for 2.5 hours. Part of the solution, 125 ml., was evaporated under reduced pressure to an amber oil. The oil was then azeotroped 3 times with 70 ml. of toluene under reduced pressure. The residue was suspended in an 80:20 H$_2$O-CH$_3$OH soultion (700 ml.) and stirred for 0.5 hour until most of the solid dissolved, then filtered. The filtrate was treated with 1.5 g. of ("Darko") charcoal for about 20 minutes. The charcoal was filtered off through a "Celite" pad. The solution was then freeze-dried in 9 separate 100 ml. round bottom flasks. The freeze-dried material weighed 2.415 g. It was recrystallized in batches of 0.200 g. as described above to yield a total of 0.923 g. 7-[D-α-amino-α-(p-hydroxyphenyl)acetamido]-3-(1,2,3-triazol-5-ylthiomethyl)-3-cephem-4-carboxylic acid. NMR was consistent, indicating the presence of ⅓ mole of CH$_3$OH. Anal. Calcd. for C$_{18}$H$_{18}$N$_6$O$_5$S$_2$·H$_2$O·1/3CH$_3$OH: C, 44.83; H, 4.38; N, 17.10; S, 13.09.
Found: C, 45.77, 44.36; H, 4.44, 4.34; N, 16.61, 16.52; S, 13.01, 13.01.

Preparation of Crystalline Methanol Solvate of 7-[D-α-amino-α(p-hydroxyphenyl)acetamido]-3-(1,2,3-triazol-5-ylthiomethyl)-3-cephem-4-carboxylic acid.

1. Fifty grams of 7-[D-α-amino-α-(p-hydroxyphenyl)-acetamido]-3-(1,2,3-triazol-5-ylthiomethyl)-3-cephem-4-carboxylic acid is slurried in 250 ml. of 95% V/V methanol/water (95% methanol) solution, at 22° -25° C.

2. Concentrated hydrochloric acid is added with rapid stirring to a pH of 1.3 - 1.5. A solution or near solution is obtained.

3. Adjust the pH to 1.7 with triethylamine.

4. Add 7.5 grams of activated charcoal ("Darco G-60") and slurry for 0.5 hours.

5. The carbon is removed by filtration and washed with 75 ml. of methanol which is added to the filtrate. Steps 2,3 and 4 should be completed within 5 hours.

6. The combined wash and filtrate of Step 5 is rapidly stirred. Triethylamine is added over a 5 minute period to pH 4.5. Crystallization starts in about 1-3 minutes. The mixture is slurried for one hour.

7. The crystals are collected by filtration, washed with 100 ml. of methanol and vacuum dried at 56° C. -24 hours. Bio yield 75-90%; bio-assay = 850-900 mcg./mg.; NMR-IR = Consistent for 1 mole of methanol; % H$_2$O, KF = 2-4.0.

Preparation of Crystalline 1,2-Propylene Glycol Solvate of
7-[D-α-amino-α(p-hydroxyphenyl)acetamido]-3-(1,2,3-triazol-5-ylthiomethyl)-3-cephem-4-carboxylic acid 1. Twenty-five grams of the methanol solvate of 7-[D-α-amino-α-(p-hydroxyphenyl)acetamido]-3-(1,2,3-triazol-5-ylthiomethyl)-3-cephem-4-carboxylic acid prepared above is slurried in 150-200 ml. of 75% V/V propylene glycol-water solution at 20° -25° C.

2. Concentrated hydrochloric acid is added to a pH of 1-1.2 to obtain a solution or near solution.

3. Triethylamine (TEA) is slowly added with rapid stirring to obtain a pH of 1.7 - 1.8.

4. Five grams of "Darco G-60" is added and the mixture is slurried for 0.5 hour. The carbon is removed by filtration (filtration is slow, an 18.5 cm. SS No. 576 paper is suggested). The carbon filter cake is washed with 40 ml. of 75% V/V propylene glycol water solution. The wash is added to the filtrate. Steps 2, 3 and 4 above should be completed within 5 hours.

5. Triethylamine is added to pH 4.5 over a 10 minute period to the rapidly stirring filtrate - wash mixture of Step 4. Crystals form in about 1-3 minutes. The mixture is slurried for one hour.

6. The crystals of the propylene glycol solvate of 7-[D-α-amino-α-(p-hydroxyphenyl)acetamido]-3-(1,2,3-triazol-5ylthiomethyl)-3-cephem-4-carboxylic acid are collected by filtration. Filtration is slow (a 12.5 - 15.0 cm. SS No. 604 paper is suggested). The crystals are washed consecutively with 50 ml. of 75% propylene glycol, 50 ml. of methanol, 50 ml. of acetone and vacuum dried at 56° C. for 24 hours. Biological yield: 80-95%. Properties of 7-[D-α-amino-α-(p-hydroxyphenyl)acetamido]-3-(1,2,3-triazol-5-ylthiomethyl)-3-cephem-4-carboxylic acid propylene glycol solvate.

a. Bio-assay = 840–900 mcg./mg.

b. IR-NMR = Consistent for a structure containing 1.0 – 1.5 MOLES of propylene glycol (15–19% propylene glycol). No loss of the 3-triazole side chain evident.

c. % Water, K.F. = 1–3.0.

d. Crystal morphology = 100% crystalline (microcrystals, triangular shaped).

e. M.P. = 182° –184° C. (D, hot stage).

f. $[\alpha]_d^{25}$ (C = 1%; 1N-HC1) = +53°.

g. Water solubility = Approximately 10 mg./ml. in water at 23° C.

h. Loss of bioactivity on storage at elevated temperatures: 100° C., 24 hours = <6%; 48 hours = <12%; 56° C., 1 month = <10%.

Preparation of Crystalline Methanol Solvate from Crystalline Propylene Glycol Solvate The propylene glycol solvate of 7-[D-α-amino-α-(p-hydroxyphenyl)acetamido]-3-(1,2,3-triazol-5-ylthiomethyl)-3-cephem-4-carboxylic acid (50 g.) as prepared above is slurried in 250 ml. of 95% (volume/volume) methanol-water solution at 22° –25° C. Concentrated HCl is added with rapid stirring to a pH of 1.1–1.5 whereupon a solution or near solution is obtained. The pH is adjusted to 1.7 with triethylamine and 7.5 g. of activated charcoal is added with slurrying for 0.5 hours. The charcoal is removed by filtration and washed with 75 ml. of methanol. The wash solution is then added to the filtrate. (The steps from addition of the HCl to this point should be completed within 5 hours). The combined wash and filtrate is rapidly stirred and triethylamine added over a 5 minute period until a pH of 4.5 is reached. Crystallization starts in about 1–3 minutes. The mixture is slurried for 1 hours, and the crystals are removed by filtration, washed with 100 ml. methanol and vacuum dried at 56° C. for 24 hours. Bio Yield 75–90%; bio-assay = 850-900 mcg./mg.; NMR-IR = consistent for 1 mole of methanol; % $H_2O$, K.F. = 2–4.0

Preparation of Crystalline 7-[D-α-amino-α-(p-hydroxyphenyl)acetamido]-3-(1,2,3-triazol-5-ylthiomethyl)-3-cephem-4-carboxylic acid sesquihydrate 7-[D-α-amino-α-(p-hydroxyphenyl)acetamido]-3-(1,2,3-triazol-5-ylthiomethyl)-3-cephem-4-carboxylic acid methanol solvate (15 g.) was slurried in 60 ml. of water. The pH was raised to 6.5 by addition of 4N NaOH and the mixture was passed through a 200 mesh screen. The reaction mixture was slurried at room temperature for 2 hours, the pH being maintained at 6.5 during this period. The crystals were removed by filtration, washed with 20 ml. of water and air dried at 37° C. for 24 hours to give 11.5 g. of title crystalline product. Bio assay = 924 mcg./mg. (average % $H_2O$, K.F. = 5.26). NMR and IR were consistent for the proposed structure and indicated that the product contained no methanol but did have a trace of propylene glycol.

Preparation of Crystalline 7-[D-α-amino-α-(p-hydroxyphenyl)acetamido]-3-(1,2,3-triazol-5-ylthiomethyl)-3-cephem-4-carboxylic acid sesquihydrate and formation of other crystalline hydrates 7-[D-α-amino-α-(p-hydroxyphenyl)acetamido]-3-(-1,2,3-triazol-5-ylthiomethyl)-3--cephem-4-carboxylic acid methanol solvate (200 mesh; 10.0 g.) substantially free of propylene glycol is slurried in 30–40 ml. of deionized water at ambient room temperature (20° –25° C.) to give a pH 3–4 aqueous suspension. NaOH (40%) is slowly added with rapid stirring to bring the pH to 6.3-6.7. The mixture is slurried at pH 6.3–6.7 for 2 hours. The crystals are removed by filtration, washed with water and air dried at room temperature for 24 hours to give a 75–80% weight yield of 950–1000 mcg./mg. crystals of 7-[D-α-amino-α-(p-hydroxyphenyl)acetamido]-3-(1,2,3-triazol-5-ylthiomethyl)-3-cephem-4-carboxylic acid dihydrate. IR and NMR analyses were consistent for the proposed structure and indicated that the product contained no methanol but did have a trace of propylene glycol. $H_2O$, K.F. = 6.56.

A sample of the crystalline dihydrate was air dried at 37° C. for 24 hours giving the crystalline sesquihydrate of 7-[D-αamino-α-(p-hydroxyphenyl)acetamido]-3-(1,2,3-triazol-5-ylthiomethyl)-3-cephem-4-carboxylic acid. $H_2O$, K.F. = 4.26.

A second sample of the dihydrate was air dried at 45° C. for 24 hours to give the crystalline sesquihydrate. $H_2O$, K.F. = 5.5.

A sample of the dihydrate was air dried at 56° C. for 24 hours to give the crystalline monohydrate of 7-[D-α-amino-α-(p-hydroxyphenyl)acetamido]-3-(1,2,3-triazol-5-ylthiomethyl)-3-cephem-4-carboxylic acid. $H_2O$, K.F. = 4.38 (theoretical % $H_2O$ for monohydrate - 3.75).

A sample of the dihydrate was vacuum dried over $P_2O_5$ at room temperature for 24 hours giving the crystalline hemihydrate of 7-D-α-amino-α-(p-hydroxyphenyl)acetamido]-3-(1,2,3-triazol-5-ylthiomethyl)-3-cephem-4-carboxylic acid. $H_2O$, K.F. = 2.63 (theoretical % $H_2O$ for hemihydrate - 1.91).

A sample of the dihydrate was vacuum dried at 56° C. for 24 hours giving the crystalline hemihydrate. $H_2O$, K.F. = 1.6–2.0.

D-(-)-2-(3'-methyl-4'-hydroxyphenyl)glycyl chloride hydrochloride is prepared in a high state of purity and very efficiently by the following procedure:

About 0.06 moles of D-(-)-2-(3'-methyl-4'-hydroxyphenyl)glycine is slurried in 100 ml. of dioxane. The slurry is stirred and $COCl_2$ (phosgene) is passed in while the slurry temperature is held at 50°–58° C. The $COCl_2$ is passed in for a total time of 3.5 hours. A yellow solution is obtained. The solution is purged with nitrogen to expel the excess $COCl_2$. HCl gas is bubbled through the solution for 2.5 hours. The solution is stirred and a small amount is diluted with some ether to obtain some crystals which are added to the batch as seed. The solution is stirred at 20°–25° C. for 16 hours. The resulting slurry of crystalline D-(-)-2-(3'-methyl-4'-hydroxyphenyl)glycyl chloride hydrochloride is filtered to collect the product. The filter-cake is washed with dioxane and methylene chloride and then dried in a vacuum desicator over $P_2O_5$ to yield about 7 g. of D-(-)-2-(3'-methyl-4'-hydroxyphenyl)glycyl chloride hydrochloride.

2-(3'-Methyl-4'-hydroxyphenyl)glycine.

A solution of 59.02 g. (0.6 mole) of 75% glyoxylic acid in 100 ml. of water was added to a suspension of 54.6 g. (0.5 mole) of 2-methylphenol and 140 ml. of conc. ammonium hydroxide in 400 ml. of water at room temperature. The temperature of the mixture rose to 37° C. The mixture was stirred at room temperature for 65 hours. The solution, initially at pH 10.1, was adjusted to pH 6.8 with 6 N hydrochloric acid causing the product to crystallize. The product was collected by filtration, washed with water and dried in vacuo over phosphorus pentoxide giving 31.5 g. (34.8%) of 2-(3'-methyl-4'-hydroxyphenyl)glycine; decomp. 196°–199° C. The infrared and nuclear magnetic resonance spectra were consistent for the desired product. Reference: Belgium Pat. No. 774,029 to Beecham Group Limited, 1972 (Farmdoc 27, 122T) which reports m.p. 205°–207° C. Anal. Calcd. for $C_9H_{11}NO_3$: C, 59.66; H, 6.13; N, 7.73. Found: C, 57.68; H 6.23; N, 7.47; $H_2O$, 2.34 Found, corrected for 2.34% $H_2O$: C, 59.06; H, 6.12; N, 7.67.

D,L-N-Chloroacetyl-2-(3'-methyl-4'-hydroxyphenyl)-glycine.

A suspension of 20.2 g. (0.112 mole) of D,L-2-(3'-methyl-4'-hydroxyphenyl)glycine in 175 ml. of water was adjusted to pH 10.3 with 20% sodium hydroxide causing a solution. The solution was cooled in an ice bath. Chloracetic anhydride (38.2 g., 0.224 mole) was added all at once and the pH of the reaction mixture was maintained at pH 10 by the addition of 20% sodium hydroxide until no further pH change was detected. The reaction mixture was stirred an additional 10 minutes in the cold. The reaction mixture was then acidified to pH 2.0 with 6N hydrochloric acid causing the product to crystallize. The product was collected by filtration, washed with water and air dried. Recrystallization from 200 ml. of hot water gave 13.7 g. (47.4%) of D,L-N-chloroacetyl-2-(3'-methyl-4'-hydroxyphenyl)glycine. The infrared and nuclear magnetic resonance spectra were consistent for the desired product. Anal. Calcd. for $C_{11}H_{12}NO_4Cl \cdot H_2O$: C, 47.92; H, 5.118; N, 5.081. Found: C, 48.11; H, 5.16; N, 5.15.

D-(-)-N-Chloroacetyl-2-(3'-methyl-4'-hydroxyphenyl)-glycine.

D,L-N-Chloroacetyl-2-(3'-methyl-4'-hydroxyphenyl)glycine (5.0 g., 0.0194 mole) and L-ephenamine acetate (6.1 g., 0.0213 mole) were dissolved in 50 ml. of isopropyl alcohol by heating on a steam bath. Water (50 ml.) was added and upon cooling, the L-ephenamine salt crystallized. The salt was collected by filtration and air dried.

The salt was suspended in 30 ml. of water and 50 ml. of methylene chloride and the mixture adjusted to pH 10.0 with 20% sodium hydroxide. The phases were separated and the aqueous phase was extracted twice more with methylene chloride.

The aqueous solution was then adjusted to pH 2.0 with 6N hydrochloric acid causing the product to crystallize. The product was collected by filtration and dried in vacuo over phosphorus pentoxide affording 0.9 g. (36.1%) of D-(-)-N-chloroacetyl-2-(3'-methyl-4'-hydroxyphenyl)glycine; m.p. 170°–172° C., $[\alpha]_D^{24}$ O = 185.9° (C 1, 95% EtOH). The infrared and nuclear magnetic resonance spectra were consistent for the desired product.

Anal. Calcd. for $C_{11}H_{12}NO_4Cl$: C, 51.27; H, 4.696; N, 5.436.

Found: C, 51.21; H, 4.77; N, 5.29.

1,2-Diphenyl-2-methylaminoethanol, commonly called ephenamine (per Federal Register, June 7, 1951) has the structure

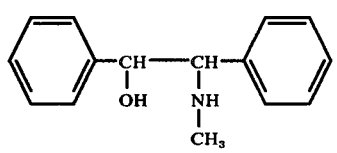

The compound is also named N-methyl-1,2-diphenyl-2-hydroxyethylamine or alpha,beta-diphenyl-beta-hydroxy-N-methylethylamine or 1,2-diphenyl-2-methylamino-1-ethanol.

This process utilizes only the levoerythro isomer. Methods for its preparation and reaction with penicillin G were described in U.S. Pat. Nos. 2,645,638 (V.V. Young) and 2,768,081 (F. H. Buckwalter). The latter reviews earlier literature as does W. B. Wheatley et al., J. Org. Chem., 18(11), 1564–1571 (1953). It was used to resolve racemic phenoxymethyl penicillin by Sheehan et al., J. Am. Chem. Soc., 81, 3089–3094 (1959); see especially p. 3091.

D-(-)-2-(3'-Methyl-4'-hydroxyphenyl)glycine

D-(-)-N-Chloroacetyl-2-(3'-methyl-4'-hydroxyphenyl)glycine (11.1 g., 0.0431 mole) was combined with 100 ml. of 2N hydrochloric acid and the mixture was refluxed for 1.5 hours. The solution was cooled and the pH adjusted to 5.0 with 20% sodium hydroxide causing the product to crystallize. The product was collected by filtration, washed with water and dried in vacuo over phosphorus pentoxide giving 7.4 g. (94.7%) of D-(-)-2-(3'-methyl-4'-hydroxyphenyl)glycine; decomp. 205°–209° C., $[\alpha]_D^{24} = -152.6°$ (C 1, 1 N HCl). The infrated and nuclear magnetic resonance spectra were consistent for the desired product.

Anal. Calcd. for $C_9H_{11}NO_3$: C, 59.66; H, 6.13; N, 7.73.

Found: C, 58.62; H, 5.49; N, 7.78; $H_2O$, 1.46.

Found, corrected for 1.46% $H_2O$: C, 59.48; H, 5.41; N, 7.84.

D-(-)-N-t-Butoxycarbonyl-2-(3'-methyl-4'-hydroxyphenyl)-glycine

To a slurry in 200 ml. of $H_2O$-dioxane (1:1) of 7.2 g. (0.0397 mole) of D-(-)-2-(3'-methyl-4'-hydroxyphenyl)glycine and 3.2 g. (0.08 mole) of powdered magnesium oxide stirred at room temperature, 9.7 g., (0.068 mole) of t-butoxycarbonyl azide was added dropwise. The reaction mixture was then heated to 42°–45° C. under a nitrogen atmosphere for 19 hours. The mixture was then diluted with 100 ml. of ice water. The solution was layered with ethyl acetate and filtered to remove some insoluble material that had separated. The aqueous phase of the filtrate was separated and extracted twice more with ethyl acetate. The aqueous solution was then adjusted to pH 5.0 with 42% phosphoric acid and extracted 5 times with ethyl acetate. The combined organic extracts were washed 3 times with water, dried over sodium sulfate and the solvent removed at reduced pressure leaving an oil. The oil was dried in vacuo over phosphorus pentoxide resulting in 10.6 g. (95%) of D-(-)-N-t-butoxycarbonyl-2-(3'-methyl-4'-hydroxyphenyl)glycine. The infrared spectrum was consistent for the desired structure.

7-[D-2-t-Butoxycarbonylamino-(3'-methyl-4'-hydroxyphenyl)acetamido]-3-(1,2,3-triazol-5-ylthiomethyl)-3-cephem-4-carboxylic acid.

A. Mixed Anhydride

A solution of 2.8 g. (0.01 mole) of D-(-)-N-t-butoxycarbonyl-2-(3'-methyl-4'-hydroxyphenyl)glycine in 100 ml. of tetrahydrofuran was cooled to −15° C. in an ice-salt-acetone bath. N-Methylmorpholine (1.01 g., 0.01 mole) was added followed by 1.37 g. (0.01 mole) of isobutyl chloroformate and the reaction mixture stirred at −15° to −20° C. for 8 minutes. A precipitate of N-methylmorpholine hydrochloride separated immediately.

B. Coupling

7-Amino-3-(1,2,3-triazol-5-ylthiomethyl)-3-cephem-4-carboxylic acid (3.1 g., 0.01 mole) was suspended in 100 ml. of water and 1.01 g. (0.01 mole) of N-methylmorpholine added. A complete solution was not obtained. Then 1,1,3,3-tetramethylguanidine was added dropwise to this stirred suspension until a clear solution was obtained. The solution was then cooled to 4° C. in an ice bath and added to the mixed anhydride solution at −15° C. The cooling bath was removed and the mixture was stirred for 1.5 hours. The tetrahydrofuran was then removed at reduced pressure and the aqueous concentrate was layered with ethyl acetate. The aqueous phase was adjusted to pH 2.0 with 42% phosphoric acid causing insoluble material to separate. The solid was removed by filtration. The aqueous phase of the filtrate was separated and extracted twice more with ethyl acetate. The combined organic extracts were washed twice with water, dried over sodium sulfate and the solvent removed at reduced pressure leaving a viscous oil residue. The oil was triturated with "Skellysolve B" containing a small amount of diethyl ether, producing a solid. This solid product was collected by filtration, washed with "Skellysolve B" and air dried. A TLC (Silica gel; solvent, 97:23 acetone-acetic acid) of the product showed the material to be a mixture of the desired product and the side-chain acid. This material was then stirred with 100 ml. of anhydrous diethyl ether for one hour. The insoluble solid was collected by filtration and air dried yielding 0.95 g. (16.4%) of 7-[D-2-t-butoxycarbonylamino-(3'-methyl-4'-hydroxyphenyl)acetamido]-3-(1,2,3-triazol-5-ylthiomethyl)-3-cephem-4-carboxylic acid. A TLC (Silica gel; solvent 97:3 acetone-acetic acid) showed this sample to contain only a trace amount of the sidechain acid. The infrared spectrum was consistent for the desired product.

7-[D-2-t-Butoxycarbonylamino-(3'-methyl-4'-hydroxyphenyl)acetamido]-3-(1,2,3-triazol-5-ylthiomethyl)-3-cephem-4-carboxylic acid.

A. Mixed Anhydride

A solution of 14.06 g. (0.05 mole) of D-(-)-N-t-butoxycarbonyl-2-(3'-methyl-4'-hydroxyphenyl)glycine in 500 ml. of tetrahydrofuran was cooled to −15° C. in an ice-salt-acetone bath. N-methylmorpholine (5.06 g., 0.05 mole) was added followed by 6.83 g. (0.05 mole) of isobutyl chloroformate and the reaction mixture stirred at −13 to −17° C. for 10 minutes. A precipitate of N-methylmorpholine hydrochloride separated immediately.

B. Silyl Ester

A mixtue of 8.0 g. (0.025 mole) of 7-amino-3-(1,2,3-triazol-5-ylthiomethyl)-3-cephem-4-carboxylic acid, 7.0 ml. (0.05 mole) of triethylamine, 6.9 ml. (0.0545 mole) of N,N-dimethylaniline, 9.5 ml. (0.075 mole) of chlorotrimethylsilane and 650 ml. of methylene chloride was heated at reflux for three hours. An additional 1.6 ml. of chlorotrimethylsilane was added after the first hour of reflux. The hazy solution was cooled and the methylene chloride removed at reduced pressure. The residue was taken up in 500 ml. of tetrahydrofuran.

C. Coupling

The silyl ester solution was cooled to 10° to 15° C. in an ice bath and added all at once to the mixed anhydride solution that was at −15° C. The cooling bath was removed and the reaction mixture stirred for two hours. Then 500 ml. of water was added and the tetrahydrofuran was removed at reduced pressure causing a gummy oil to separate. The oil was extracted into ethyl acetate and the phases separated. The aqueous phase (pH 3.8) was layered with ethyl acetate causing some solid to separate. This precipitate was removed by filtration and the aqueous phase of the filtrate separated. The aqueous solution was adjusted to pH 2.3 with 42% phosphoric acid and extracted again with ethyl acetate. The combined ethyl acetate extracts were washed 3 times with water, dried over sodium sulfate and the solvent removed at reduced pressure leaving a viscous oil. The oil was stirred with 100 ml. of anhydrous diethyl ether for 1.5 hours producing a solid. The product was filtered, washed sparingly wth anhydrous diethyl ether and air dried. A TLC (silica gel; solvent, 99:1 acetone-acetic acid) of the product showed the material was a mixture of the desired product, the sidechain acid and a third unidentified component. The material was stirred again in 100 ml. of anhydrous diethyl ether for 1.5 hours. The insoluble solid was collected by filtration and air dried giving 10.7 g. (74.4%) of 7-[D-2-t-butoxycarbonylamino-(3'-methyl-4'-hydroxyphenyl)acetamido]-3-(1,2,3-triazol-5-ylthiomethyl)-3-cephem-4-carboxylic acid. A TLC (silica gel; solvent, 99:1 acetone-acetic acid) showed this sample to contain only a trace amount of the sidechain acid and a third unidentified component. The infrared spectrum was consistent for the desired product.

7-[D-2-t-Butoxycarbonylamino-(3'-methyl-4'-hydroxyphenyl)acetamido]-3-(1,2,3-triazol-5-ylthiomethyl)-3-cephem-4-carboxylic acid.

Mixed Anhydride

A solution of 12.2 g. (0.0434 mole) of D-(−)-N-t-butoxycarbonyl-2-(3'-methyl-4'-hydroxyphenyl)glycine in 425 ml. of tetrahydrofuran was cooled to −15° C. in an ice-salt-acetone bath. n-methylmorpholine (4.35 g., 0.0434 mole) was added followed by 5.87 g. (0.0434 mole) of isobutyl chloroformate and the reaction mixture stirred at −15° C. for 10 minutes. A precipitate of N-methylmorpholine hydrochloride separated immediately.

B. Silyl Ester

A mixture of 6.8 g. (0.0217 mole) of 7-amino-3-(1,2,3-triazol-5-ylthiomethyl)-3-cephem-4-carboxylic acid, 6.02 ml. (0.043 mole) of triethylamine, 6.0 ml. (0.0473 mole) of N,N-dimethylaniline, 8.26 ml. (0.0651 mole) of chlorotrimethylsilane and 550 ml. of methylene chloride was heated at reflux for 2 hours. The hazy solution was cooled and the methylene chloride removed at reduced pressure. The residue was taken up in 425 ml. of tetrahydrofuran.

C. Coupling

The silyl ester solution was cooled to 10° C. in an ice bath and added all at once to the mixed anhydride solution that was at −15° C. The cooling bath was removed and the reaction mixture stirred for 2 hours. Then 425 ml. of water was added and the mixture stirred for 5 minutes. The tetrahydrofuran was removed at reduced pressure causing a gummy oil to separate. The oil extracted into ethyl acetate and some insoluble solid that had separated was removed by filtration. The aqueous phase of the filtrate was separated, adjusted to pH 2.0 with 42% phosphoric acid and extracted twice more with ethyl acetate. The combined ethyl acetate extracts were washed three times with water, dried over sodium sulfate and the solvent removed at reduced pressure leaving a viscous oil. The oil was dissolved in 30 ml. of acetone and this solution was added dropwise to a well-stirred 300 ml. volume of anhydrous diethyl ether. The mixture was stirred at room temperature for 2.5 hours. The insoluble solid that had separated was collected by filtration and air dried. A TLC (silica gel; solvent, 99:1 acetone-acetic acid) of the product showed the material was a mixture of the desired product, the sidechain acid and a third unidentified component. The solid was stirred again in 80 ml. of anhydrous diethyl ether for one hour. The insoluble material was collected by filtration, washed sparingly with anhydrous diethyl ether and air dried giving 5.8 g. (46.5%) of 7-[D-2-t-butoxycarbonylamino-(3'-methyl-4'-hydroxyphenyl)acetamido]-3-(1,2,3-triazol-5-ylthiomethyl)-3-cephem-4-carboxylic acid. A TLC (silica gel; solvent, 99:1 acetone-acetic acid) showed this sample to contain only a trace of the sidechain acid and a third unidentified component. The infrared spectrum was consistent for the desired product.

7-[D-2-amino-(3'-methyl-4'-hydroxyphenyl)acetamido]-3-(1,2,3-triazol-5-ylthiomethyl)-3-cephem-4-carboxylic acid 7-[D-2-t-butoxycarbonylamino-(3'-methyl-4'-hydroxyphenyl)acetamido]-3-(1,2,3-triazol-5-ylthiomethyl)-3-cephem-4-carboxylic acid (0.95 g., 0.002 mole) was added to 15 ml. of cold trifluoroacetic acid and the solution was stirred for 15 minutes. The trifluoroacetic acid solution was then poured into 200 ml. of 2:1 "Skellysolve B"-anhydrous diethyl ether and the mixture cooled. The precipitated trifluoroacetic acid salt of the product, 7-[D-2-amino-(3'-methyl-4'-hydroxyphenyl)acetamido]-3-(1,2,3-triazol-5-ylthiomethyl)-3-cephem-4-carboxylic acid, was collected by filtration, washed with 2:1 "Skellysolve B" anhydrous diethyl ether and dried in vacuo over phosphorus pentoxide yielding 0.75 g. of material.

The salt (0.75 g.) was suspended in 50 ml. of water, 25 ml. of Amberlite La-1 resin acetate form (25% in methyl isobutyl ketone) and 25 ml. of methyl isobutyl ketone and stirred at room temperature for two hours.

The phases were separated and the methyl isobutyl ketone layer was extracted once with water. The aqueous phases were combined and then extracted 8 times with diethyl ether. The aqueous phase was filtered and the solvent removed at reduced pressure. The residue was triturated with methyl isobutyl ketone to produce a solid. The material was collected by filtration, washed with methyl isobutyl ketone, acetone and dried at 65° C. in vacuo over phosphorus pentoxide giving 0.36 g. (59.0%) of 7-[D-2-amino-(3'-methyl-4'-hydroxyphenyl)acetamido]-3-(1,2,3-triazol-5-ylthiomethyl)-3-cephem-4-carboxylic acid; decomp. >150° C. The infrared and nuclear magnetic resonance spectra were consistent for the desired product.

LA-1 resin is a mixture of secondary amines wherein each secondary amine has the formula

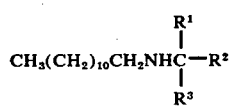

wherein each of $R^1$, $R^2$ and $R^3$ is a monovalent aliphatic hydrocarbon radical and wherein $R^1$, $R^2$ and $R^3$ contain in the aggregate from eleven to fourteen carbon atoms. This particular mixture of secondary amines, which is sometimes referred to herein as "Liquid Amine Mixture No. II", is a clear amber liquid having the following physical characteristics: viscosity at 25° C. of 70 cpd., specific gravity at 20° C. of 0.826; refractive index at 25° C. of 1.4554; distillation range at 10 mm., up to 170° C. − 0.5%, 170°–220° C. - 3%, 220°–230° C. - 90% and above 230° C. - 6.5%.

7-[D-2-amino-(3'-methyl-4'-hydroxyphenyl)acetamido]-3-(1,2,3-triazol-5-ylthiomethyl)-3-cephem-4-carboxylic acid is also called BL-S638.

2-(3'-Methoxy-4'-hydroxyphenyl)glycine.

A solution of 59.2 g (0.6 mole) of 75% glyoxylic acid in 100 ml. of water was added to a suspension of 62.07 g. (0.5 mole) of 2-methoxyphenol and 140 ml. of concentrated ammonium hydroxide in 400 ml. of water at room temperature. The temperature of the mixture rose to 35° C. The mixture was stirred at room temperature for 65 hours. The product that had crystallized was collected by filtration, washed with water, then acetone and dried in vacuo over phosphorus pentoxide giving 57.4 g. (58.2%) of 2-(3'-methoxy-4'-hydroxyphenyl)glycine; decomp. 218°–220° C. (Lit. 240° C.). The infrared and nuclear magnetic resonance spectra were consistent for the desired product.

Anal. Calcd. for $C_9H_{11}NO_4$: C, 54.82; H, 5.62; N, 7.10.

Found: C, 53.77; H, 5.91, N, 6.97; $H_2O$, 1.13

Found, corrected for 1.13% $H_2O$: C, 54.38; H, 5.85; N, 7.05. Reference: B. Block, Z. Physiol. Chem., 98, 226 (1917).

Resolution of 2-(3'-Methoxy-4'-hydroxyphenyl)glycine

A. Methyl 2-(3'-Methoxy-4'hydroxyphenyl)glycinate

A cooled suspension of 94 g. (0.476 mole) of 2-(3'-methoxy-4'hydroxyphenyl)glycine in 500 ml. of absolute methanol was gassed at a rapid rate with HCl for 20 minutes. At first a clear solution was obtained and then crystalline product separated in quantity. After 20 hours the methyl ester hydrochloride was filtered and washed sparingly with methanol; 99.6 g. after air drying. A cooled solution of the hydrochloride in 800 ml. of water was adjusted to pH 8 (NaOH) giving a crystalline precipitate of the ester free base; 81.3 g. The IR and NMR spectra were consistent.

Anal Calcd. for $C_{10}H_{13}NO_4$: C, 56.86; H, 6.20; N, 6.63.

Found: C, 56.46; H, 6.28; N, 6.55; $H_2O$, 0.59.

B. D-(-)-2-(3'-Methoxy-4'-hydroxyphenyl)glycine.

A mixture of 50 g. (0.237 mole) of methyl 2-(3'-methoxy-4'-hydroxyphenyl)glycinate, 19 ml. (0.333 mole) of acetic acid and 1 liter of i-PrOH (isopropyl alcohol) was heated to boiling giving a partial solution. Dibenzoyl-d-tartaric acid monohydrate (89.2 g., 0.237 mole) was added with good stirring and then the mixture was refluxed. Soon the salt started to crystallize. The heat was shut off and the flask was allowed to cool slowly to room temperature. After cooling in an ice bath the precipitate was collected by filtration. The filtrate was concentrated to about one-third of its initial volume giving a small second crop of salt; total yield of both crops 54.1 g. after air drying (solid A; see below).

The filtrate was concentrated free of solvent. The viscous residue was combined with 300 ml. of 1N HCl and the mixture extracted with 400 ml. of $CHCl_3$. The $CHCl_3$ phase was extracted twice with 100 ml. portions of 1 N HCl. The combined HCl extracts were concentrated briefly to remove residual $CHCl_3$ and refluxed for 1 hour. The solution was concentrated to a small volume causing the amino acid HCl salt to crystallize. The product was collected by filtration and recrystallized from 50 ml. of 1N HCl. A solution of the product in 200 ml. of water was adjusted to pH 4.5 (NaOH). The mixture was heated nearly to boiling and allowed to cool to precipitate D-(−)-2-(3'-methoxy-4'-hydroxyphenyl)glycine as fluffy needle-like crystals. After cooling overnight, the product was collected by filtration, washed sparingly with water and methanol and dried at 40° C.; 8.7 g., $[\alpha]24°$ D =−136.5° (c 1 1N HCl). The IR and NMR spectra were fully consistent.

Anal. Calcd. for $C_9H_{11}NO_4 \cdot H_2O$: C, 50.23; H, 6.09; N, 6.51; $H_2O$, 8.37.

Found: C, 50.43; H, 6.23; N, 6.51; $H_2O$, 8.95.

C. L-(+)-2-(3'-methoxyl-4'-hydroxyphenyl) glycine

Solid A above (54.1 g.) was suspended in 300 ml. of 1N HCl and 500 ml. of $CHCl_3$ with good agitation. The salt did not break up readily in this system, therefore, the $CHCl_3$ was separated as well as possible and 300 ml. of MIBK added with good agitation. The MIBK phase was extracted with an additional 200 ml. of 1N HCl in 3 portions. The combined and filtered HCl extracts were concentrated briefly to remove residual solvents and heated at reflux for 1 hour to hydrolyze the ester. The reaction mixture was concentrated to small volume. After cooling in an ice bath the crystalline amino acid HCl salt was collected by filtration. The salt was recrystallized from 75 ml. of 1 N HCl, dissolved in 500 ml. of water by warming, the solution polish filtered and adjusted to pH 4.5 (NaOH) causing the zwitterion to crystallize. The mixture was heated to boiling, filtered, and stored in the cold to precipitate the crystalline product, L-(+)-2-(3'-methoxy-4'-hydroxyphenyl)glycine. The product was collected by filtration, washed sparingly with water and methanol and dried at 40° C.; 9.6 g., $[\alpha]24°D = +127.2°$ ( c 1 1N HCl). The IR and NMR spectra were consistent.

Anal. Calcd. for $C_9H_{11}NO_4 \cdot H_2O$: C, 50.23; H, 6.09; N, 6.51; $H_2O$, 8.37.

Found: C, 50.53; H, 6.06; N, 6.62; $H_2O$, 7.46. Sodium D-N-(2-methoxycarbonyl-1-methylvinyl-α-amino-α- (3'-methoxy-4'-hydroxyphenyl)acetate.

To a stirred solution of 3.02 g. (0.078 mole) of NaOH in 320 ml. of methanol is added 0.08 mole of D-(−) -2-(3'-methoxy-4'-hydroxyphenyl)glycine and the resulting mixture is heated at reflux while a solution of 9.6 ml. (0.088 mole) of methyl acetoacetate in 80 ml. of methanol is added over a thirty-minute period. After an additional 30 minutes refluxing, the methanol is distilled off while toluene is added at the same rate so as to keep approximately the same internal volume. When the internal temperature reaches 100° C. the suspension is cooled in ice water for 4 hours, filtered, washed well with toluene, air dried and vacuum dried over $P_2O_5$ to constant weight to yield solid sodium D-N-(2-methoxy- carbonyl-1-methylvinyl)-α-amino-α-(3'-methoxy-4'- hydroxyphenyl)acetate. D-(−) -2-(3'-methoxy-4'-hydroxyphenyl)glycly chloride hydrochloride is prepared in a high state of purity and very efficiently by the following procedure:

About 0.06 moles of D-(−) -2-(3'-methoxy- 4'-hydroxyphenyl)glycine is slurried in 100 ml. of dioxane. The slurry is stirred and $COCl_2$ (phosgene) is passed in while the slurry temperature is held at 50–58° C. The $COCl2_2$ is passed in for a total time of 3.5 hours. A yellow solution is obtained. The solution is purged with nitrogen to expel the excess $COCl_2$. HCl is bubbled through the solution for 2.5 hours. The solution is stirred and a small amount is diluted with some ether to obtain some crystals which are added to the batch as seed. The solution is stirred at 20°–25° C. for 16 hours. The resulting slurry of crystalline D-(−)-2-(3'-methoxy-4'-hydroxy- phenyl)glycyl chloride hydrochloride is filtered to collect the product. The filtercake is washed with dioxane and methylene chloride and then dried in a vacuum desicator over $P_2O_5$ to yield about 7 g. of D-(−)-2-(3'-methoxy-4'-hydroxyphenyl)glycyl chloride hydrochloride.

D-(−)-N-(t-butoxycarbonyl)-2-(3'-methoxy-4'-hydroxy- phenyl)glycine.

A mixture of 8.6 g. (0.04 mole) of D-(=)- 2-(3'-methoxy-4'-hydroxyphenyl)glycine, 3.2 g. (0.08 mole) of magnesium oxide, 9.7 g. (0.068 mole) of t- butoxycarbonyl azide and 240 ml. of 1:1 dioxane- water was stirred and heated at 45°–50∞ C. for 20 hours under a nitrogen atmosphere. The cooled reaction mixture was diluted with 240 ml. of ice water, filtered and extracted once with ethyl acetate. The acidified (pH 2) aqueous phase was extracted 5 times with ethyl acetate. The combined and dried ($Na_2SO_4$) ethyl acetate extracts were concentrated free of solvent at reduced pressure giving the product as a viscous oil; 6.3 g.

Resolution of 2-(3-Methoxy-4-hydroxyphenyl)glycine.

A. (−) -2-(3-Methoxy-4-hydroxyphenyl)glycine d-10-Camphorsulfonate.

A mixture of 5.0 g. of 2-(3- methoxy-4-hydroxyphenyl)glycine, 50 ml. of glacial acetic acid and 2.5 ml. of $H_2O$ was heated giving a solution. The hot solution was polish filtered and stored at room temperature for 18 hours to crystallize giving 1.78 g. of the salt. Recrystallization from 15 ml. of acetic acid followed by drying at 40° C. afforded 1.54 g. of (−)-2-(3-methoxy-4-hydroxyphenyl)- glycine d-10-camphorsulfonate; partial decomp. 164–170° C. then decomp. 175–180° C., $[\alpha]24°D°=−35.3°(C\ 1\ H_2O)$.

The combined acetic acid filtrates were concentrated to a small volume at reduced pressure. The crystalline solid was filtered and recrystallized from 15 ml. of acetic acid giving, after drying at 40° C., a second crop of product; 2.48 g., decomp. 164°–170°, $[\alpha]24°D$ =−32.2° (C 1 $H_2O$).

B. (−)-2-(3-Methoxy-4-hydroxyphenyl)glycine

A 1.2 g portion of the first crop of (−)-2-(3-methoxy-4-hydroxyphenyl)glycine d-10-camphorsulfonate was dissolved in 12 ml. of water and the solution adjusted to pH 4.5 with dilute aqueous $NH_4OH$. The mixture was heated giving a soltution was allowed to cool at first at room temperature then at 5° C. to crystallize the amino acid. The product was filtered, washed sparingly with a few drops of water and methanol and dried at 40° C. giving 0.37 g. of (−)-2-(3- methoxy-4-hydroxyphenyl)glycine; decomp. 210°–212°, $[\alpha]24°D$ =−137.6°(C 1 1N HCl).

Anal. Calcd. for C₉H₁₁NO₄: C, 54.82; H, 5.62; N, 7.10.

Found: C, 54.37; H, 5.90; N, 7.21; H₂O, 0.71.

C. (−)-2-(3-Methoxy-4-hydroxyphenyl)glycine.

A mixture of 200 g. of 2-(3-methoxy-4-hydroxyphenyl)- glycine hydrate, 260 g. of d-10-camphorsulfonic acid, 2 l. of glacial acetic acid and 100 ml. of water was heated to give a solution and polish filtered. The solution was seeded and stored at room temperature for three days to crystallize the salt; 76 g. The salt was recrystallized from 400 ml. of acetic acid; 71.0 g.

The filtrate fron the first crop of salt was concentrated to about one-half of its initial volume and the product allowed to crystallize; 118.5 g. The product was recrystallized from 500 ml. of acetic acid giving, after air drying, 105.2 g. of (−)-2-(3-methoxy-4-hydroxyphenyl)glycine d-10- camphorsulfonate.

Concentrated NH₄OH was added dropwise with good stirring to a solution of 71.0 g. of the camphorsulfonate salt in 150 ml. of water plus 150 ml. of methanol. The mixture which soon became very thick was warmed to 50° C. and the dropwise addition of NH₅OH continued to pH 4.5 After ice-cooling the product was filtered, washed sparingly with cold 1:1 MeOH-water and cold methanol giving, after drying in a vacuum oven at 40° C., 34.5 g. (−) -2-(3-methoxy-4- hydroxyphenyl)glycine; decomp. 204–206° C., [α]22°D =−132.4° (C 1 1N HCl).

Anal. Calcd. for C₉H₁₁NO₄·H₂O: C, 50.23; H, 6.09; N, 6.51.

Found: C, 49.96; H, 6.12; N, 6.61.

(−)-2-(3,4-Dihydroxyphenyl)glycine

A mixture of 9.2 g. of (−)-2-(3-methoxy-4-hydroxyphenyl)glycine and 50 ml. of 48% hydrobromic acid was heated at reflux for 4 hours. The solution was cooled in ice giving a crystalline precipitate which was collected by filtration and dried at 40° C.; yield 1.8 g., m.p. 248°–250° C. dec. with prior darkening above ca. 200° C., [α]22°D =−42.1° (C 1 H₂O). Anal. Calcd. for C₈H₉NO₄·HBr·½H₂O: C, 35.18; H, 4.06; N, 5.13; H₂O; 3.30. Found: C, 35.26; H, 4.01; N, 5,32; H₂O 3.20. This material was concluded to be a 3:1 composition of (−) and (+) isomers of 2-(3,4- dihydroxyphenyl)glycine HBr.

The filtrate was concentrated to a small volume. The crystalline mass which separated was collected by filtration (the filtrate was retained). The crude product was recrystallized from 20 ml. acetic acid. The product was washed on the filter with methyl isobutyl ketone and anhydrous ether giving 3.0 g. white crystalline (−)-2-(3,4-dihydroxyphenyl) glycine hydrobromide; m.p. 106°–109° C., [α]22°D =−85.0° (C 1 H₂O).

Anal. Calcd. for C₈H₉NO₄·HBr·H₂O: C, 34.06; H, 4.29;

N, 4,97; H₂O, 6.37. Found: C, 43.07; H, 4.17; N, 4.99; H₂O, 6.80.

The acetic acid filtrate was concentrated free of solvent. To the oily residue was added 75 ml. methyl isobutyl ketone and the product allowed to crystallize first at room temperature and then in an ice bath. The product was filtered, washed with methyl isobutyl ketone and anhydrous ether giving an additional 1.5 g. of white crystalline (−) -2-(3,4- dihydroxyphenyl)glycine hydrobromide; m.p. 106°–108°C., [α]22°D =−84.5° (C 1 H₂O).

Anal. Calcd. for C₈H₉NO₄·HBr·H₂O: C, 34.06; H, 4.29;

N, 4.97; H₂O, 6.39. Found: C, 33.79; H, 4.31; N, 4.94; H₂O, 7.08.

The filtrate from the crude HBr salt was concentrated free of solvent. The crystalline residue was dissolved in 8 ml. of water and the solution adjusted to pH 4.5 with concentrated aqueous NH₄OH causing the zwitterion to crystallize. The mixture was diluted with an equal volume of methanol and cooled in ice for one-half hour. The product, (−)-2-(3,4-dihydroxyphenyl)glycine, was filtered, washed sparingly with 1:1 MeOH-H₂ O and MeOH, and dried for 2 hours at 40° C.; yield, 0.536 g., indistinct decomp. 234°–238° C. with prior darkening above ca. 220° C., [α]$_d^{22°}$=−158.2° (C 1 1N HCl). Anal.

Anal. Calcd. for C₈H₉NO₄: C, 52.46; H, 4.95; N, 7.65. Found: C, 51.82; H, 5.03; N, 7.75.

7-[D-α-amino-(3′-methoxy-4′-hydroxyphenyl)acetamido]- 3-(1,2,3-triazol-4-ylthiomethyl)-3-cephem-4-carboxylic acid.

A mixture of 4.27 g. (0.01365 mole) of 7- amino-3-(1,2,3-triazol-4-ylthiomethyl)-3-cephem-4- carboxylic acid, 6.64 g. (0.041 mole) of 1,1,1,3,3,3- hexamethyldisilazane and 200 ml. of methylene chloride was heated at reflux for 4 hours giving a clear solution. After storing overnight at room temperature the solvent was removed at reduced pressure. The residue was dissolved in 150 ml. of tetrahydrofuran and the solution cooled to 0 to 5° C. prior to use.

N-methylmorpholine (3.06 ml., 0.0273 mole) and 3.48 ml. (0.0273 mole) of isobutyl chloroformate were added to a solution of 8.1 g. (0.0273 mole) of D-(−)-N-(t-butoxycarbonyl)-2-(3′-methoxy-4′-hydroxy- phenyl)glycine in 300 ml. of tetrahydrofuran at −15° C. The mixture was stirred at −15° C. for 6 minutes to form the mixed anhydride.

The tetrahydrofuran solution of the silyl ester at 0° to 5° C. was added to the mixed anhydride at −15° C. After 10 minutes the cooling bath was removed and the mixture stirred 2.5 hours longer. Water (250ml.) was added to the reaction mixture and the mixture concentrated at reduced pressure to remove most of the tetrahydrofuran. The aqueous concentrate was acidified with 42% phosphoric acid and extracted 3 times with ethyl acetate. The mixture was filtered during the first extraction to remove a small amount of insoluble material. The combined ethyl acetate extracts were washed once with water, dried (Na₂SO₄) and concentrated to dryness. The residue was triturated with anhydrous ether giving 2.8 g. of solid.

A solution of the solid (2.8 g.) and 50 ml. of 97% formic acid was stirred at room temperature for 2 hours. The formic acid was distilled off at reduced pressure. The residue was azeotroped with toluene to completely remove formic acid. The residue was triturated with wt ethyl acetate giving (after drying for 2 hours, in vacuo at 65° C. over phosphorus pentoxide) 1.42 g. of 7-[D-α-amino-(3′-methoxy-4′-hydroxyphenyl)- acetamido]-3-(1,2,3-triazol-4-ylthiomethyl)-3-cephem- 4-carboxylic acid; decomp. gradually above about 165° C. The IR and NMR spectra were consistent, 7-[D-α-amino-(3′-methoxy-4′-hydroxyphenyl)acetamido]- 3-(1,2,3-triazol-4-ylthiomethyl)-3-cephem-4-carboxylic acid is also called BL-S689.

The compounds of the present invention are prepared by reaction of an aldehyde having the structure $R_2$-CHO (wherein $R^2$ is as defined above) with a cephalosporin having the formula

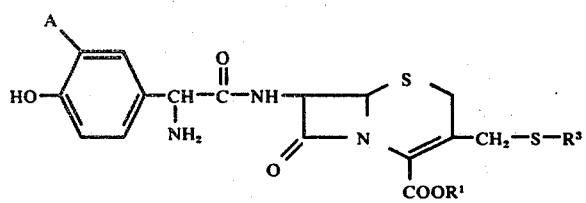

wherein A, $R^1$ and $R^3$ have the meaning set forth above. In the preferred embodiments the carbon bearing the $\alpha$-amino group has the D configuration. The latter compounds of formula II are prepared by the general, and often specific, procedures set forth in the following patents:

U.S. 3,899,394
U.S. 3,855,213
U.S. 3,867,380
South Africa 73/4055
Belgium 776,222 (Farmdoc 38983T)
Belgium 810,477 (Farmdoc 57268V)
West Germany 2,364,192 (Farmdoc 49048V)
West Germany 2,500,386 (Farmdoc 49692W)
Belgium 814,727 (Farmdoc 82562V)
West Germany 2,404,592 (Farmdoc 57268V)

An alternative method of perparing the amphoteric cephalosporins used as starting materials herein consits of substituting the appropriate p-hydroxy-2- phenylglycine (which may contain an additional substituent and in which the $\alpha$-amino group is suitably protected during acylation in a conventional manner) for the sidechain acid, e.g. 2-phenylglycine or tetrazoleacetic acid, previously used as in U.S. Pat. No. 3,813,388 and 3,759,904 and 3,850,916 to make either 3-thiolated cephalosporins or to make 7-substituted cephalosporanic acids in which the 3-acetoxy group is then displaced by the desired thiol. For examples see U.S. Pat. Nos. 3,757,012 and 3,757,015.

Reference below to BL-S640 refers to 7-[D-$\alpha$-amino-$\alpha$-(p-hydroxyphenyl)acetamido]-3-(1,2,3-triazol- 5-ylthiomethyl)-3-cephem-4-carboxylic acid which is also called cefatrizine. Reference to the propylene glycolate thereof refers to the 1,2-propylene glycol solvate described above.

The following examples are given in illustration of, but not in limitation of, the present invention.

DESCRIPTION OF THE PREFERRED EMBODIMENTS

EXAMPLE 1

Reaction Product of BL-S640 and 5-Formyl-2-Furansulfonic Acid-Sodium Salt (BL-S1027)

Formula (BL-S1027)

PROCEDURE FOR PREPARATION

II

1. Slurry 9.0 grams of 5-formyl-2-furansulfonic acid-sodium salt

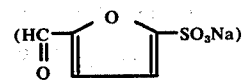

in 75 ml. of water at 60° C.
2. Twenty grams (1 equivalent) of BL-S640 1,2-propylene glycol adduct is sprinkled in with rapid stirring over a 10 minute period with concomitant adjusting of the pH to 6–7.0. A solution or near solution forms.
3. The solution is stirred at 55°–$\alpha$° C., pH 6–7.0 for 10 minutes and then cooled to 4°–8° C. A small amount of precipitate forms.
4. The mixture is stirred for 15 minutes at 4°–8°0 C. and then filtered.
5. The filtrate is added over a 5 minute interval to 1 liter of rapidly stirring isopropanol. A heavy precipitate forms. The mixture is slurried for 5 minutes.
6. The solids are removed by filtration, washed with 200 ml. of isopropanol and vacuum dried at 56° C. for 24 hours.
7. The solids are dissolved in 60 ml. of 4°–6° C. water (a small amount of insolubles are removed by filtration). The filtrate is lyophilized for 24 hours. Yield: 23 grams; Bio yield = 89%.

PROPERTIES OF BL-S1027

1. Bioassay as BL-S640 = 724 mcg/mg. (Theory = 750 mcg/mg.).
2. Solubility = >500 mg/ml.
3. IR-NMR: Consistent for structure. At 70 mg/ml., compound exists as 80% cyclic, 20% non cyclic derivative.
4. Paper strip and liquid chromatography indicate product at 0.2 and 1.0 mg./ml. water solution exists as free BL-S640.
5. MIC bacterial spectrum is equal to that of BL-S640.
6. Oral and intramuscular rat blood levels are equal to that of BL-S640.
7. A solution of this product in water at a concentration of 25,000 mcg./ml. was stable (retained full bioactivity) for at least three days at room temperature and

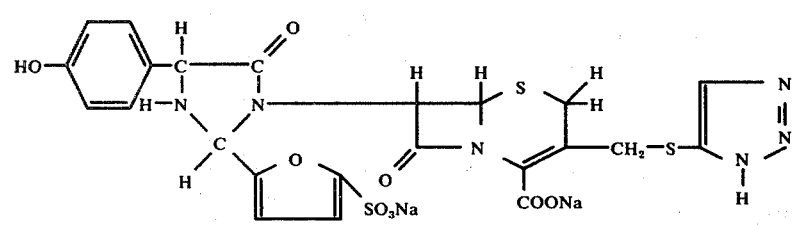

for 14 days at 6° C. (refrigerator) thus providing a solution suitable for oral use.

ANALYTICAL DATA

| % H₂O | — | Found 5.14 | Dry basis | Theory |
|---|---|---|---|---|
| C | — | 40.15 | 42.1 | 43.0 |
| H | — | 3.10 | 2.9 | 2.96 |
| N | — | 12.39 | 13.05 | 13.1 |
| S | — | 13.6 | 14.35 | 14.95 |
| Ash as Na | — | 5.86 | 6.16 | 6.8 for di Na |

Table I

Antibiotic Activity In Nutrient Broth

| Organism | | MIC (mcg./ml.) | | |
|---|---|---|---|---|
| | | Sodium Salt Cpd of Ex. 1[1] | BL-S640[2] | Cephalothin |
| Str. pneumoniae* A9585 | (10⁻³)** | 0.03 | 0.13 | 0.03 |
| Str. pyogenes A9604 | (10⁻³)** | 0.03 | 0.06 | 0.03 |
| S. aureus Smith A9537 | (10⁻⁴) | 0.27 | 0.5 | 0.13 |
| S. aureus + 50% serum A9537 | (10⁻⁴) | 2 | 4 | 0.5 |
| S. aureus BX1633 A9606 | (10⁻³) | 0.5 | 0.5 | 0.13 |
| S. aureus BX1633 A9606 | (10⁻³) | 4 | 4 | 0.25 |
| Meth-Res A15097 | (10⁻⁴) | 4–8 | 8–16 | 1–16 |
| Sal. enteritidis A9531 | (10⁻⁴) | 0.25 | 0.25 | 0.25 |
| E. coli Juhl A15119 | (10⁻⁴) | 1 | 1 | 16 |
| E. coli A9675 | (10⁻⁴) | 4 | 4 | 32 |
| K. pneumoniae A9977 | (10⁻⁴) | 0.5 | 0.5 | 1 |
| K. pneumoniae A15130 | (10⁻⁴) | 1 | 2 | 32 |
| Pr. mirabilis A9900 | (10⁻⁴) | 0.5 | 0.5 | 1 |
| Pr. morganii A15153 | (10⁻⁴) | 32 | 63 | >125 |
| Ps. aeruginosa A9843A | (10⁻⁴) | >125 | >125 | >125 |
| Ser. marcescens | (10⁻⁴) | >125 | >125 | >125 |
| Ent. cloacae A20019 | (10⁻⁴) | >125 | >125 | >125 |
| Ent. cloacae A9656 | (10⁻⁴) | 1 | 1 | 8 |
| Ent. cloacae A9657 | (10⁻⁴) | 32 | 63 | >125 |
| | A9659 | | | |

\* 45% AAB + 5% serum + 50% broth listed above.
\*\* Dilution of overnight broth culture.
[1]These figures were recalculated on the basis that there was only 65% BL-S640 in the sample; in other words, the numerical values were lowered, i.e. improved.
[2]BL-S640 = 7-[D-α-amino-α-(p-hydroxyphenyl)acetamido]-3-(1,2,3-triazol-5-ylthiomethyl)-3-cephem-4-carboxylic acid.

Table II

Mouse Blood Levels After Oral Administration Of 100 mg./kg. Body Weight

| Compound | Blood Level (μg/ml.) | | | |
|---|---|---|---|---|
| | 0.5 | 1 | 2 | 3.5 |
| | Hrs. After Administration | | | |
| Compound of Ex. 1 | 45 | 36.6 | 20.4 | 10.4 |
| BL-S640[1] | 50.5 | 39 | 24.5 | 9.6 |
| Compound of Ex. 1 | 54.6 | 53.5 | 27.6 | 8.2 |
| BL-S640[1] | 57.4 | 47 | 29.5 | 10.9 |

The compounds were prepared in Tween - carboxymethylcellulose and 8 mice were used for each compound

[1]BL-S640 - 7-[D-α-amino-α-(p-hydroxypehnyl)acetamido]-3-(1,2,3-triazol-5-ylthiomethyl)-3-cephem-4-carboxylic acid was used as a standard.

BL-S1027 is the water soluble derivative formed when BL-S640 is reacted with furfural sodium sulfonate. The bio potency is 724 mcg./mg. of BL-S640 activity.

Aqueous solutions containing 250, 25 and 10 mg. BL-S640 activity/ml. as BL-S1027 may be stored under refrigeration (4° C.) or at room temperature for at least 24 hours with no significant loss in activity.

Table III

Mouse Blood Levels After Intramuscular Administration of 10 mg./kg. Body Weight

| Compound | 0.25 | 0.5 | 1 | 1.5 |
|---|---|---|---|---|
| | Hours after Administration | | | |
| Compound of Example 1 | 16.1 | 14.8 | 11.9 | 8 |
| | 14.6 | 15.4 | 11.7 | 8.3 |
| BL-S640[1] | 16.3 | 13.5 | 9.4 | 6.3 |

[1]BL-S640 - 7-[D-α-amino-α-(p-hydroxyphenyl)acetamido]-3-(1,2,3-triazol-5-ylthiomethyl)-3-cephem-4-carboxylic acid was used as a standard. The compounds were dissolved in 0.01% phosphate buffer.

EXAMPLE 2

Reaction Product of BL-S640 and o-Formylphenoxyacetic acid. (BL-S1048)

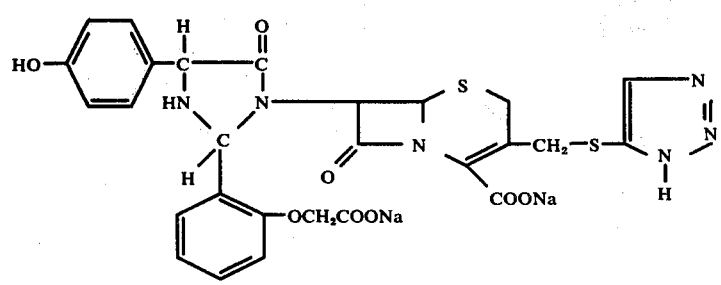

Procedure for Preparation 1. 375 mg. of o-formylphenoxyacetic acid

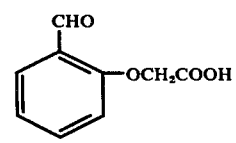

is slurried in 10 ml. of water and 4 N NaOH is added with rapid stirring to pH 7.0. A solution is obtained.

2. 2 g. (1 equivalent) of BL-S640 methanol adduct is added with rapid stirring over a 10 minute interval with concomitant of 4 N NaOH to a pH of 6 – 6.5. A solution or near solution is obtained.

3. The solution is filtered and held at ambient room temperature for 0.5 hour.

4. The solution is lyophilized for 24 hours to give the product as a solid.

Properties of Solid Product

1. IR-NMR (70 mg./ml.) Consistent for structure, triazole and β-lactam intact.

2. Paper strip and liquid chromatography at 0.2 and 1 mg./ml. show BL-S640 completely free of the aldehyde.

| Analytical Data | | | |
|---|---|---|---|
| | Found | Dry Basis | Theory |
| % Water | 4.06 | — | — |
| C | 47.15 | 49.2 | 50.1 |
| H | 3.79 | 3.5 | 3.86 |
| N | 11.44 | 11.93 | 13.0 |
| S | 8.87 | 9.27 | 9.91 |
| Ash as Na | 5.55 | 5.78 | 6.47 |

3. Solubility in water = >400 gm./ml.

| Compound | No. of Mice | 0.5 | 1 | 2 | 3.5 |
|---|---|---|---|---|---|
| | | Hr. After Administration | | | |
| BL-S1027 | 16 | 49.8 | 45.1 | 24 | 9.3 |
| BL-S1048 | 16 | 46.5 | 44.6 | 28.1 | 12.8 |
| BL-S640 | 32 | 53.4 | 45.4 | 27.2 | 10.7 |

The compounds were prepared in Tween-CMC. BL-S640 was used as standard for all compounds.

Urinary Recovery After IM Administration of 50 and 10 mg./kg. to Rats

| Compound | Dose (mg./kg.) | No. of Rats | Percentage of Administered Dose Recovered | | |
|---|---|---|---|---|---|
| | | | 0–6 | 6–24 | 0–24 |
| | | | Hr. After Administration | | |
| BL-S1027 | 50 | 4 | 39.6 | 2.6 | 42.2 |
| | 10 | 4 | 30.1 | 1.7 | 31.8 |
| BL-S1048 | 50 | 4 | 32.3 | 2.4 | 34.7 |
| | 10 | 4 | 21.7 | 2 | 23.7 |
| BL-S640 | 50 | 7 | 44.5 | 2.7 | 47.2 |
| | 10 | 7 | 24.3 | 1.4 | 25.7 |

The compounds were prepared in 0.01% phosphate buffer. BL-S640 was used as standard for all compounds.

Paper chromatograms were run on rat urine collected between 0 and 2 and between 2 and 4 hours following IM administration (at 10 mgm./kg. and at 50 mgm./kg.) of BL-S1027, 1048 and 640, for the detection of antibiotically active metabolites using descending chromatography with system No. 9 (butyl acetate:n-butanol:glacial acetic acid:$H_2O$ = 80:15:40:24). Two identical spots were observed in all cases other than the standard (not from the animal) which showed a single identical spot. This indicates complete hydrolysis of the two derivatives to the parent compound (BL-S640).

Antibiotic Spectrum Nutrient Broth

| Organism | | | MIC (mcg./ml.) | | |
|---|---|---|---|---|---|
| | | | BL-S640 | BL-S1027[1] | BL-S1048[2] |
| S. pneumoniae* | ($10^{-3}$) | **A9585 | 0.06 | 0.03 | 0.06 |
| Str. pyogenes* | ($10^{-3}$) | **A9604 | 0.03 | 0.03 | 0.03 |
| S. aureus Smith | ($10^{-4}$) | A9537 | 0.13 | 0.25 | 0.13 |
| S. aureus +50% serum | ($10^{-4}$) | A9537 | 2 | 2 | 2 |
| S. aureus BX1633 | ($10^{-3}$) | A9606 | 0.25 | 0.5 | 0.25 |
| S. aureus BX1633 | ($10^{-2}$) | A9606 | 4 | 4 | 2 |
| S. aureus Meth-Res | ($10^{-3}$) | A15097 | 8 | 4 | 4 |
| Sal. enteritidis | ($10^{-4}$) | A9531 | 0.25 | 0.25 | 0.13 |
| E. coli Juhl | ($10^{-4}$) | A15119 | 0.5 | 1 | 0.5 |
| E. coli | ($10^{-4}$) | A9675 | 2 | 4 | 2 |
| K. pneumoniae | ($10^{-4}$) | A9977 | 0.5 | 0.5 | 0.5 |
| K. pneumoniae | ($10^{-4}$) | A15130 | 1 | 1 | 1 |
| Pr. mirabilis | ($10^{-4}$) | A9900 | 0.5 | 0.5 | 0.5 |
| Pr. morganii | ($10^{-4}$) | A15153 | 32 | 32 | 32 |
| Ps. aeruginosa | ($10^{-4}$) | A9843A | >125 | >125 | >125 |
| Ser. marcescens | ($10^{-4}$) | A20019 | >125 | 125 | >125 |
| Ent. cloacae | ($10^{-4}$) | A9656 | >125 | >125 | >125 |
| Ent. cloacae | ($10^{-4}$) | A9657 | 0.5 | 1 | 0.5 |
| Ent. cloacae | ($10^{-4}$) | A9659 | 32 | 32 | 32 |

* 45% AAB + 5% serum +50% broth listed above.
**Dilution of overnight broth culture.

[1] Adjusted for 68% content of BL-S640
[2] Adjusted for 67% content of BL-S640
In other words, the numerical values are lowered, i.e. improved. This adjustment was also made in the tests reported below or, in the alternative, a larger weight was used to provide equivalent dosage.

Mouse Blood Levels After IM Administration of 10 mg./kg. Body Weight

| Compound | No. of Mice | 0.25 | 0.5 | 1 | 1.5 |
|---|---|---|---|---|---|
| | | Blood Levels (mcg./ml.) | | | |
| | | Hr. After Administration | | | |
| BL-S1027 | 16 | 15.4 | 15.1 | 11.8 | 8.2 |
| BL-S1048 | 16 | 14.8 | 14.1 | 10.3 | 7 |
| BL-S640 | 32 | 15.7 | 13.2 | 9.5 | 6.8 |

The compounds were prepared in 0.01% phosphate buffer. BL-S640 was used as standard for all compounds.

Mouse Blood Levels After PO Administration of 100 mg./kg. Body Weight
Blood Levels (mcg./ml.)

EXAMPLE 3

Reaction Product of BL-S640 and o-Benzaldehydesulfonic acid

[Chemical structure diagram showing BL-S640 reaction product with o-benzaldehydesulfonic acid, featuring a β-lactam ring system with HO-phenyl group, HN-CH-C linkage with o-sulfonated benzaldehyde (SO₃Na), thiazole-containing side chain with CH₂S linkage to triazole ring, and COONa group]

Procedure for Preparation

1. Eight hundred and seventy mg. of o-benzaldehyde-sulfonic acid — sodium salt was dissolved in 10 ml. of water.

2. 2 g. of BL-S640 methanol adduct (1 equivalent) was added with rapid stirring over a 10 minute interval with the concomitant addition of 4 N — NaOH to a pH of 6.5. A solution was obtained.

3. The solution was filtered, kept at room temperature for 1 hr. and lyophilized for 24 hours to give the desired product as a solid.

Properties of Product

1) IR-NMR = Well defined, consistent for structure.
2) Solubility in water = > 400 mg./ml.
3) Analytical Data

|          | Found | Dry Basis | Theory |
|----------|-------|-----------|--------|
| % Water  | 3.49  | —         | —      |
| C        | 41.88 | 43.4      | 43.3   |
| H        | 3.41  | 3.3       | 3.25   |
| N        | 11.53 | 12.1      | 12.35  |
| S        | 13.74 | 14.25     | 14.24  |
| Ash as Na| 5.45  | 5.63      | 6.77   |

4) Bio-Assay = 700 mcg./mgm.
5) IR - NMR =  a) Intact β-lactam and triazole moiety
   b) Compound does not appear to be a cyclic adduct
6) Paper Strip Chromatography: There appears to be a double zone at the $R_f$ of BL-S640.
7) Liquid Chromatography

| Time in Hours | % Free BL-S640 |
|---------------|----------------|
| 0             | 64.0           |
| 1             | 70.5           |
| 2             | 88.0           |

8) Solublility in Water = greater than 400 mg./ml.
9) Number - This product is called BL-S1055.

Antibiotic Spectrum in Nutrient Broth

|  |  |  | MIC (mcg./ml.) | |
|---|---|---|---|---|
| Organism | | | BL-S1055[(1)] | BL-S640 |
| S. pneumoniae* | $(10^{-3})$ | **A9585 | 0.06 | 0.03 |
| Str. pyogenes* | $(10^{-3})$ | **A9604 | 0.016 | 0.03 |
| S. aureus Smith | $(10^{-4})$ | A9537 | 0.13 | 0.13 |
| S. aureus +50% serum | $(10^{-4})$ | A9537 | 2 | 2 |
| S. aureus BX1633 | $(10^{-3})$ | A9606 | 0.5 | 0.13 |
| S. aureus BX1633 | $(10^{-2})$ | A9606 | 2 | 2 |
| S. aureus Meth-Res | $(10^{-3})$ | A15097 | 4 | 2 |
| Sal. enteritidis | $(10^{-4})$ | A9531 | 0.35 | 0.13 |
| E. coli Juhl | $(10^{-4})$ | A15119 | 1 | 0.5 |
| E. coli | $(10^{-4})$ | A9675 | 4 | 2 |
| K. pneumoniae | $(10^{-4})$ | A9977 | 0.5 | 0.5 |
| K. pneumoniae | $(10^{-4})$ | A15130 | 1 | 1 |
| Pr. mirabilis | $(10^{-4})$ | A9900 | 0.5 | 0.5 |
| Pr. morganii | $(10^{-4})$ | A15153 | 32 | 16 |
| Ps. aeruginosa | $(10^{-4})$ | A9843A | >125 | >125 |
| Ser. marcescens | $(10^{-4})$ | A20019 | 125 | 63 |
| Ent. cloacae | $(10^{-4})$ | A9656 | 125 | 63 |
| Ent. cloacae | $(10^{-4})$ | A9657 | 0.5 | 0.5 |
| Ent. cloacae | $(10^{-4})$ | A9659 | 63 | 63 |

*45% AAB + 5% serum + 50% broth listed above.
**Dilution of overnight broth culture.
[(1)]Adjusted for 65% content of BL-640
In other words, the numerical values are lowered, i.e. improved. This adjustment was also made in the tests reported below or, in the alternative, a larger weight was used to provide equivalent dosage.

Mouse Blood Levels After IM Administration of 10 mg./kg. Body Weight

| Compound | Blood Levels (mcg./ml.) | | | |
|----------|------|------|------|------|
|          | 0.25 | 0.5  | 1    | 1.5  |
|          | Hr. After Administration | | | |
| BL-S1055[1] | 10.3 | 9.9  | 7.6  | 6.5 |
| BL-S640     | 12.7 | 11.5 | 8    | 5.7 |

The compounds were prepared in 0.01% phosphate buffer.
Values are the average of 3 experiments
[1]BL-S640 was used as standard

Mouse Blood Levels After PO Administration of 100 mg./kg. Body Weight

| Compound | Blood Levels (mcg./ml.) | | | |
|----------|------|------|------|------|
|          | 0.5  | 1    | 2    | 3.5  |
|          | Hr. After Administration | | | |
| BL-S1055[1] | 38.2 | 35.7 | 22.0 | 11.3 |
| BL-S640     | 48.7 | 42.4 | 24.0 | 10.1 |

The compounds were prepared in Tween-CMC. Values are the average of two experiments
[1]BL-S640 was used as standard

Urinary Recovery after IM Administration of 50 mg./kg. to Rats

Percentage of Administered Dose Recovered

-continued

| Compound | No. of Rats | 0–6 | 6–24 | 0–24 |
|---|---|---|---|---|
| | | Hr. After Administration | | |
| BL-S1055[1] | 3 | 36.6 | 2.4 | 39 |
| BL-S640 | 4 | 44.2 | 3.3 | 47.5 |

The compounds were prepared in 0.01% phosphate buffer.
[1]BL-S640 was used as standard Paper chromatograms were run on rat urine collected between 0 and 2 and between 2 and 4 hours following IM administration of BL-S1055 and 640, for the detection of antibiotically active metabolites using descending chromatography with system No. 9 (butyl acetate:n-butanol:glacial acetic acid:$H_2O$ = 80:15:40:24). A single, identical spot was observed in all cases. This indicates complete hydrolysis of the derivative to the parent compound (BL-S640).

Comparative Oral $PD_{50}$ Values of
BL-S640 Derivatives in Mice

| Organism | $PD_{50}$ (mg./kg./treatment)* | | | | |
|---|---|---|---|---|---|
| | BL-S 640 | BL-S 1027 | BL-S 1048 | BL-S 1055 | Cephalexin |
| E. coli A15119 | 1.4 | — | 3.1 | 1.8 | 13 |
| | 4.1 | — | 1.6 | 1.6 | 13 |
| P. mirabilis A9900 | 7.2 | 6.3 | 4.7 | 8.2 | 66 |
| | 9.6 | 2.7 | 3.6 | 8.2 | 55 |
| P. mirabilis A9707 | 2.4 | 1.8 | 2.4 | 1 | 50 |
| K. pneumoniae A9977 | 1.6 | — | 0.7 | 1.6 | 43 |
| S. pyogenes A9604 | 0.4 | — | 0.2 | 0.4 | 11 |

*Mice were treated at 1 and 3.5 hours post-challenge.

Comparative IM $PD_{50}$ Values of
BL-S640 Derivatives in Mice

| Organism | $PD_{50}$ (mg.kg./treatment)* | | | | |
|---|---|---|---|---|---|
| | BL-S 640 | BL-S 1027 | BL-S 1048 | BL-S 1055 | Cephalexin |
| P. mirabilis A9900 | — | — | — | — | — |
| | 1.6 | 1.6 | 1.6 | 1.6 | 50 |

EXAMPLE 4

BL-S1027; The Reaction Product of BL-S640 and 5-Formyl-2-furansulfonic Acid

Structure: BL-S1027

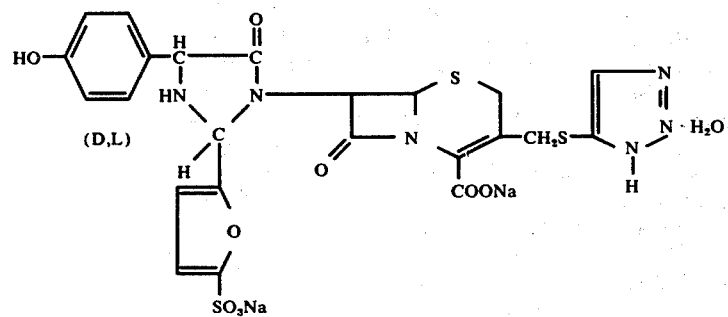

Preparation of BL-S1027

1. Nine grams of 5-formyl-2-furansulfonic acid sodium salt

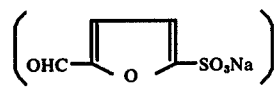

is rapidly stirred in 75 ml. of water at 60°–65° C. Most of the solids dissolve.

2. Twenty grams of BL-S640 propylene glycol adduct is sprinkled in with rapid stirring over a 10 minute interval with concomitant adjustment of the pH to 6.5–7.0 with 40% NaOH (so not allow pH to rise over 7.2). A solution or near solution forms.

3. Stir the pH 6.5–7.0 solution at 55°–60° C. for 15 minutes and cool to 4°–8° C. Stir at 4°–8° C. for 10 minutes.

4. Filter to remove a small amount of insolubles.

5. Add the filtrate* (SEE NOTE 1) rapid stirring to one liter of isopropanol. An amorphous precipitate forms. Stir for 5 minutes.

6. Remove the solids by filtration, wash with 100 ml. of isopropanol and vacuum-dry at 50-56° C. for 18 hours.

7. Dissolve the solids in 60 ml. of water and cool to 4°–6° C. A very small amount of precipitate may form and is removed by coarse filtration.

8. Pass the filtrate at ambient temperature through suitable filters to remove particles, pyrogens and bacteria.

Steps 7 and 8 should be completed within 4 hours.

9. Lyophilize sterilely for 48 hours and then heat at 50°–56° C. under vacuum for 18-23 hours. Yield of BL-S1027 is approximately 22-24 grams.

*NOTE 1, Step 5: If 18.7 grams of BL-S640 methanol adduct is substituted for the 20 grams of BL-S640 propylene glycol adduct, the filtrate may be cooled to 4–6° C. coarse filtered and lyophilized directly as described in step 8–9.

Properties of BL-S1027
1) Bio-assay = 724 mcg./mg.
2) Bio-yield = 85-95%
3) IR - NMR = a) Consistent for structure
   b) Approximately 80% cyclic, 20% noncyclic in $D_2O$, at 70 mg./ml.
   c) Approximately 0.05 mole of isopropanol.
4) Paper strip chromatography (0.2 mg./ml.) = 100% BL-S640, no evidence of derivative.
5) Liquid chromatography (1 mg./ml. in pH 7 phosphate buffer) =
   0 time = 85% free BL-S640
   0.5 hour = 94% free BL-S640
   1.0 hour = 100% free BL-S640
6) Water solubility = >400 mg./ml.
7) Analytical Data

| | Found | Dry Basis | Theory |
|---|---|---|---|
| % $H_2O$ KF | 5.14 | — | — |
| % C | 40.15 | 42.1 | 43.0 |

| % H | 3.10 | 2.9 | 2.96 |
| % N | 12.39 | 13.05 | 13.1 |
| % S | 13.6 | 14.33 | 14.95 |
| % ash as Na | 5.86 | 6.16 | 6.5 |

8) Mouse blood levels = oral and intramuscular levels approximately equal to BL-S640 propylene glycol adduct. BL-S640 appeared in urine with no evidence of the derivative.

9) a) Stability of Solids = less than 10% loss for 1 month at 56° C.
b) Stability of solutions: less than 10% loss at 250, 25 and 10 mg./ml. of BL-S640 activity for at least 24 hours at room temperature.

EXAMPLE 5

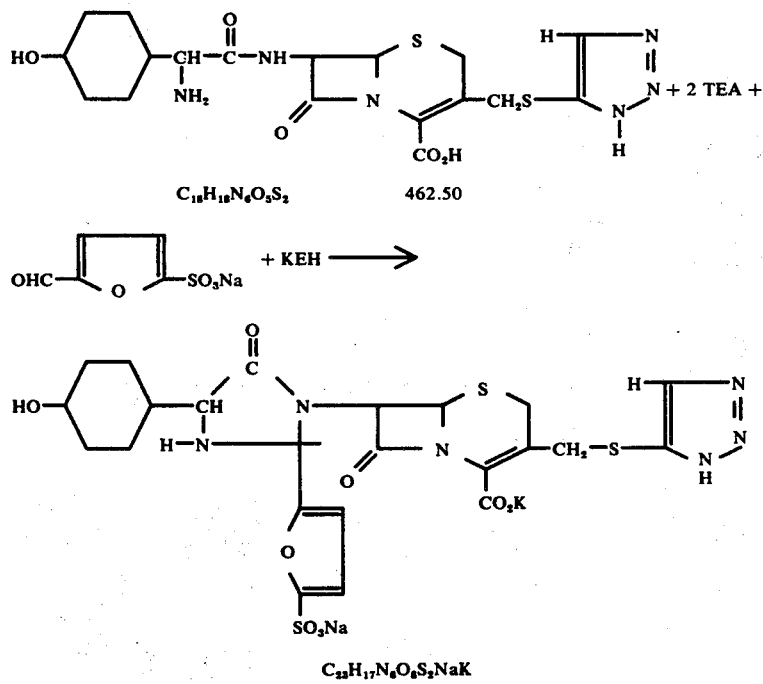

Materials:
1 g. (.00217 mole) BL-S640
429 mg. (0.0217 mole) 5-furfural sulfonic acid Na salt
217 mg (0.0434 mole) triethylamine
1.2 g. (0.0434 mole) potassium 2-ethylhexanoate (KEH)

Procedure: To a suspension of 1 g. of BL-S640 in 8 ml. of methanol was added 217 mg. of triethylamine (TEA) and 429 gm. of 5 -furfural sulfonic acid. The mixture was heated to reflux and soon all the solids dissolved. The solution was heated for 3 minutes and 1.2 g. of KEH was added. A yellow salt separated and was collected and washed with methanol. The salt was dried over $P_2O_5$ in a desicator. Yield 800 l mg. Analysis Calculated for: $C_{23}H_{17}N_6O_8S_2Nak \cdot 4H_2O$; C, 37.54; H, 3.41; N, 11.42. Found: C, 37.30; H, 3.31; N 10.18.mp >140° C. decomp.

The same reaction was run as above with the exception that sodium 2-ethylhexanoate was used in place of KEH. The salt did not precipitate out of methanol so the solution was filtered and the filtrate was diluted with isopropyl alcohol. The solid precipitate was collected and washed with isopropyl alcohol. The salt was hydroscopic so it was dried in vacuo over $P_2O_5$. Yield: 800 mg., mp >140° C. decomp.

Analysis Calculated for: $C_{23}H_{17}N_6O_8S_3Na_2$ C, 42,65; H, 2.78; N, 13.65. Found: C, 41.03; H, 3.94; N, 10.54.

The sample was soluble in water. The solution showed a pH of 6.5.

The paper strip assay in buffer and human serum was run. The sample was found to exhibit only one spot corresponding to BL-S640. Both samples exhibited a solubility of >100 mg./ml. at pH 6.5.

Paper strip chromatography showed that the above compound was completely hydrolyzed to BL-S640 in pooled human serum at pH 7 and 0.1 M phosphate buffer at pH 7. Paper strip bioautographs were run in the following manner. Samples were dissolved at a concentration of 500 γ/ml. in .1M pH 7 phosphate buffer and pH 7 pooled human serum at 500 γ/ml. A 10 μl sample of BL-S640 and the above product were spotted on a ½ inch strip of What. No. 1 paper and developed at 27° for 16 hours in a butyl acetate 80, n-butanol 15, acetic acid 40, and water 24 system. The strips were air-dried, and placed on an agar plate seeded with B. subtilis A.T.C.C. 6633. At intervals of 30 minutes, 1 hour, 3 hours and 6 hours a single zone of $R_f$ .3 was shown for all samples.

High pressure liquid chromatography at a concentration of 1 mg./ml. showed complete hydrolysis to the parent BL-S640 after one half hour. Samples were chromatographed on a μ Bondapak C18 (Waters Associates) column using a 0.01M sodium acetate pH 4/methanol 8/2 mobile phase at a flow rate of 0.52 ml./min. Detection was by UV at 354 μm. Samples were dissolved at a concentration of 1 mg./ml. in the mobile phase, 2 μ were injected and BL-S640 was eluted at 18 min. and the aldehyde at 6 min. The quantitation of BL-S640 and 5-formylfuransulfonic acid were made using p-toluene-sulfonic acid as an internal standard.

EXAMPLE 6

Compounds of the formula

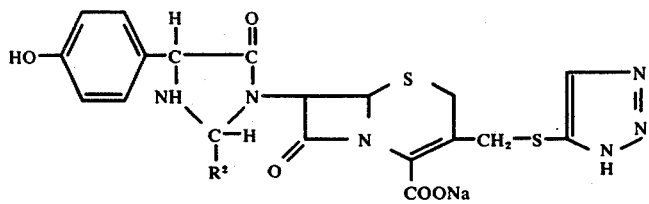

wherein $R^2$ is phenyl-2-sulfonic acid, 4-methoxyphenyl-3-sulfonic acid, 4-hydroxyphenyl-3-sulfonic acid, 2-carboxymethoxyphenyl, 4-carboxymethoxyphenyl, 3-hydroxy-4-carboxyphenyl, 4-(2'-carboxy)vinylphenyl, carboxyl, 2-carboxyphenyl, 3-carboxyphenyl, methanesulfonic acid, and methanedisulfonic acid respectively are prepared by replacing the 5-formyl-2-furansulfonic acid in the procedure of Example 1 with an equimolar weight of the corresponding aldehyde having the formula $R^2$-CHO.

EXAMPLE 7

The compounds having the formulae wherein $R^2$ is

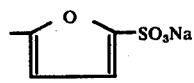

are prepared by substituting an equimolar weight of the corresponding amphoteric cephalosporin for the cefatrizine in the procedure of Example 1.

EXAMPLE 8

The compounds having the formulae

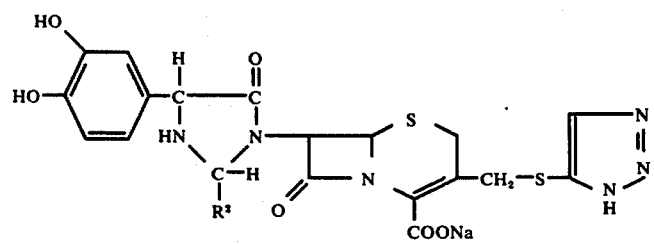

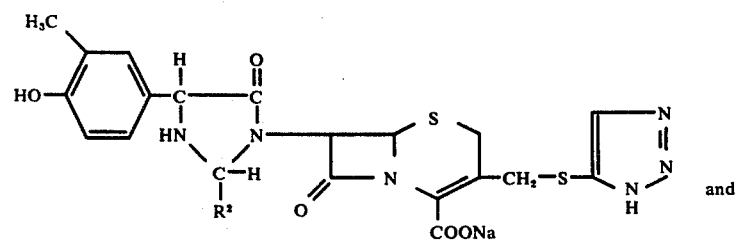

and

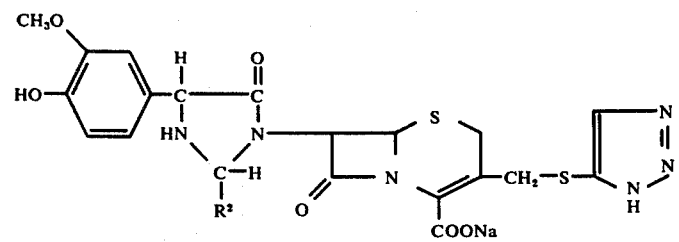

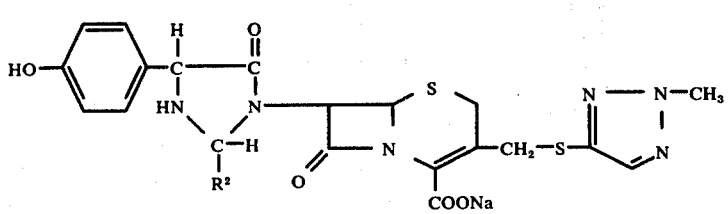

-continued
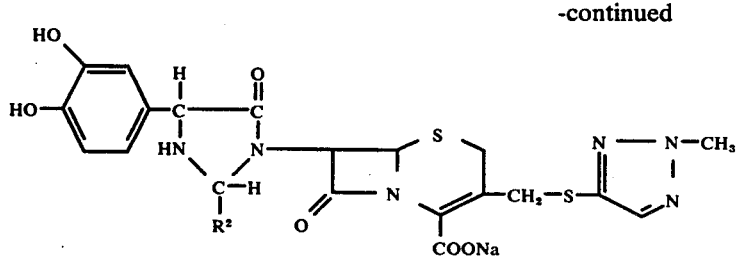
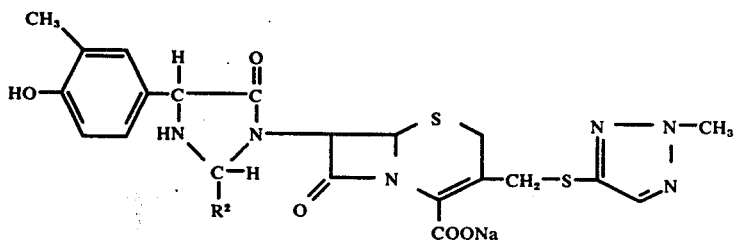
and
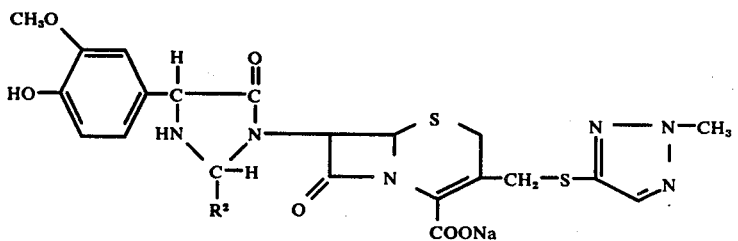
wherein R² is
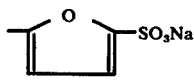
are prepared by substituting an equimolar weight of the corresponding amphoteric cephalosporin for the cefatrizine in the procedure of Example 1.
EXAMPLE 9
The compounds having the formulae
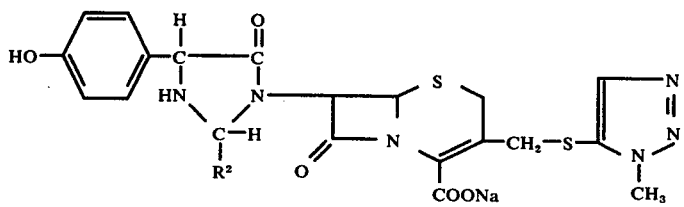
,
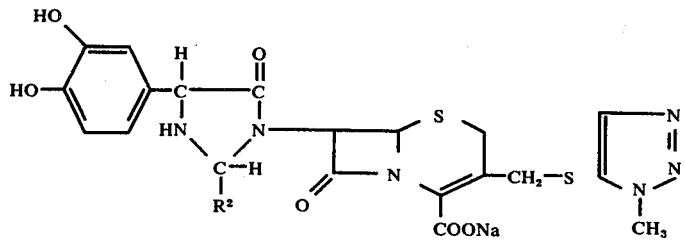
,
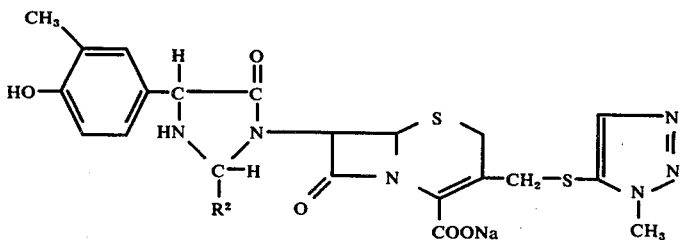
and

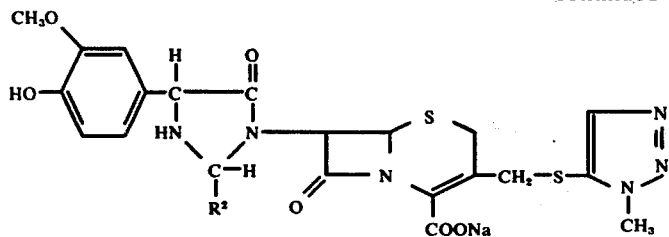

wherein R² is

are prepared by substituting an equimolar weight of the corresponding amphoteric cephalosporin for the cefatrizine in the procedure of Example 1.

EXAMPLE 10

The compounds having the formulae wherein R² is phenyl-2-sulfonic acid, 4-methoxyphenyl-3-sulfonic acid, 4-hydroxyphenyl-3-sulfonic acid, 2-carboxymethoxyphenyl, 4-carboxymethoxyphenyl, 3-hydroxy-4-carboxyphenyl, 4-(2'-carboxy)vinylphenyl, carboxyl, 2-carboxyphenyl, 3-carboxyphenyl, methanesulfonic acid, and methanedisulfonic acid respectively are prepared by replacing the 5-formyl-2-furansulfonic acid in the procedure of Example 1 with an equimolar weight of the corresponding aldehyde having the formula R²—CHO.

EXAMPLE 11

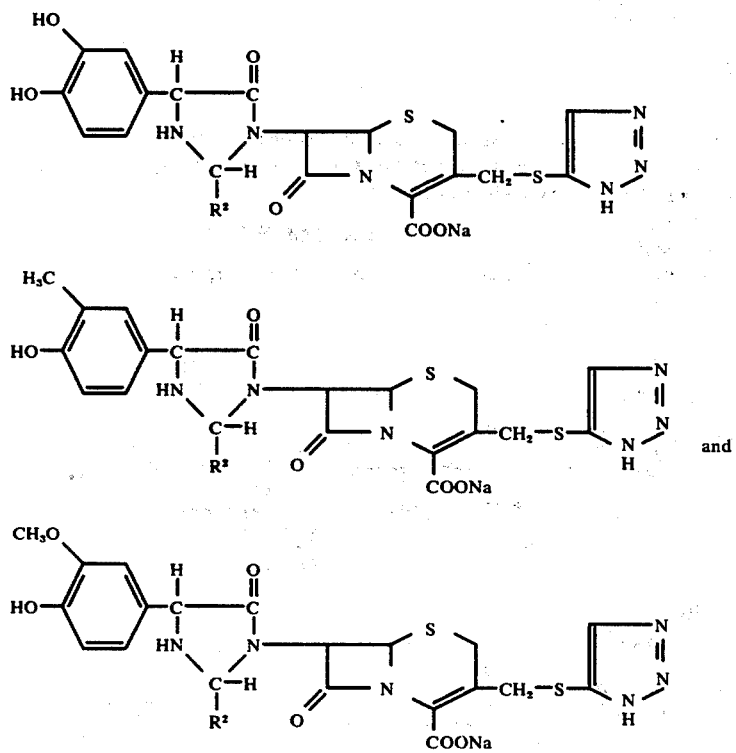

and

The compounds having the formulae

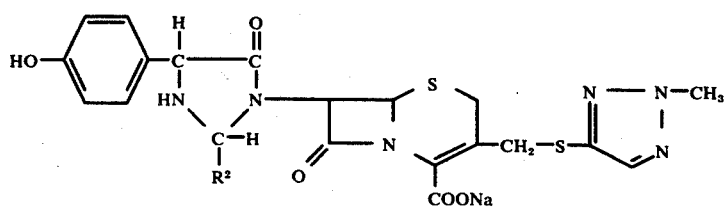

-continued

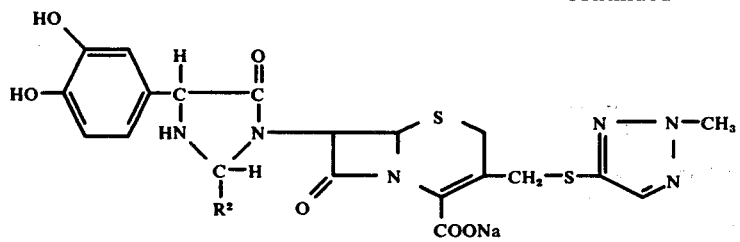

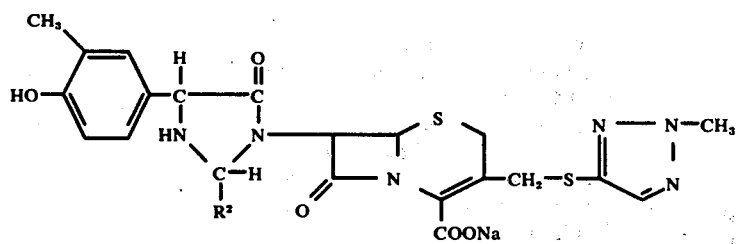

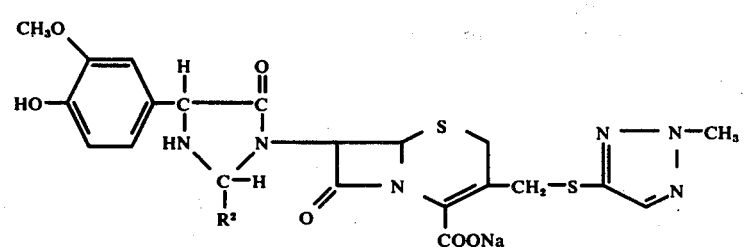

wherein $R^2$ is phenyl-2-sulfonic acid, 4-methoxyphenyl-3-sulfonic acid, 4-hydroxyphenyl-3-sulfonic acid, 2-carboxymethoxyphenyl, 4-carboxymethoxyphenyl, 3-hydroxy-4-carboxyphenyl, 4-(2'-carboxy)vinylphenyl, carboxyl, 2-carboxyphenyl, 3-carboxyphenyl, methanesulfonic acid, and methanedisulfonic acid respectively are prepared by replacing the 5-formyl-2-furansulfonic acid in the procedure of Example 1 with an equimolar weight of the corresponding aldehyde having the formula $R^2$—CHO.

EXAMPLE 12

The compounds having the formulae

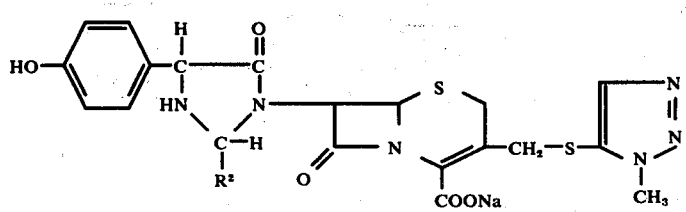

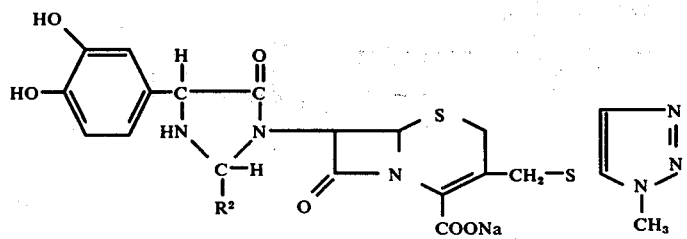

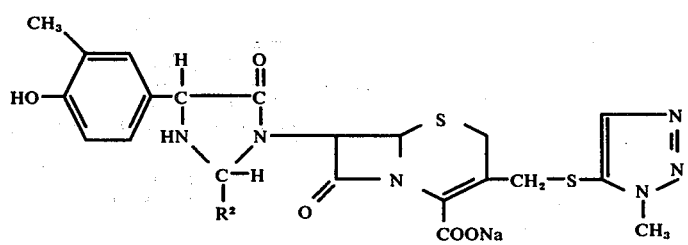

and

-continued

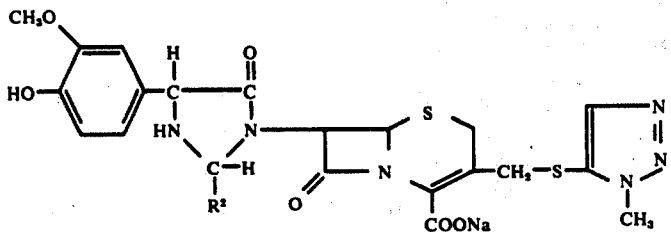

wherein $R^2$ is phenyl-2-sulfonic acid, 4-methoxyphenyl-3-sulfonic acid, 4-hydroxyphenyl-3-sulfonic acid, 2-carboxymethoxyphenyl, 4-carboxymethoxyphenyl, 3-hydroxy-4-carboxyphenyl, 4-(2'-carboxy)vinylphenyl, carboxyl, 2-carboxyphenyl, 3-carboxyphenyl, methanesulfonic acid, and methanedisulfonic acid respectively are prepared by replacing the 5-formyl-2-furansulfonic acid in the procedure of Example 1 with an equimolar weight of the corresponding aldehyde having the formula $R^2$-CHO.

We claim:

1. A compound of the formula

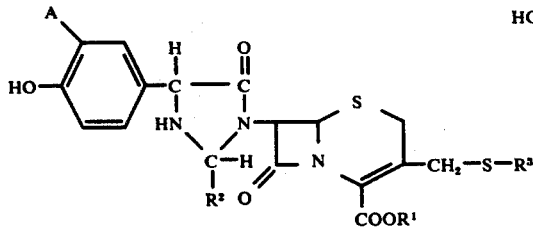

wherein
A is hydrogen, hydroxy, methyl or methoxy,
$R^1$ is hydrogen, sodium or potassium,
$R^2$ is a member selected from the group consisting of 2-furan-5-sulfonic acid, phenyl-2-sulfonic acid, 4-methoxyphenyl-3-sulfonic acid, 4-hydroxyphenyl-3-sulfonic acid, 2-carboxymethoxyphenyl, 4-carboxymethoxyphenyl, 3-hydroxy-4-carboxyphenyl, 4-(2'-carboxy)vinylphenyl, carboxyl, 2-carboxyphenyl, 3-carboxyphenyl, methanesulfonic acid and methanedisulfonic acid in the form of its sodium or potassium salt, and
$R^3$ is, 1,2,3-triazol-5-yl, such group being unsubstituted or substituted with one or two lower alkyl groups of one to four carbon atoms.

2. A compound of claim 1 wherein $R^2$ is 2-furan-5-sulfonic acid.

3. A compound of claim 1 wherein $R^2$ is phenyl-2-sulfonic acid.

4. A compound of claim 1 wherein $R^2$ is 4-methoxyphenyl-3-sulfonic acid.

5. A compound of claim 1 wherein $R^2$ is 4-hydroxyphenyl-3-sulfonic acid.

6. A compound of claim 1 wherein $R^2$ is 2-carboxymethoxyphenyl.

7. A compound of claim 1 wherein $R^2$ is 4-carboxymethoxyphenyl.

8. A compound of claim 1 wherein $R^2$ is 3-hydroxy-4-carboxyphenyl.

9. A compound of claim 1 wherein $R^2$ is 4-(2'-carboxy)vinylphenyl.

10. A compound of claim 1 wherein $R^2$ is carboxyl.

11. A compound of claim 1 wherein $R^2$ is 2-carboxyphenyl.

12. A compound of claim 1 wherein $R^2$ is 3-carboxyphenyl.

13. A compound of claim 1 wherein $R^2$ is methanesulfonic acid.

14. A compound of claim 1 wherein $R^2$ is methanedisulfonic acid.

15. A compound of the formula

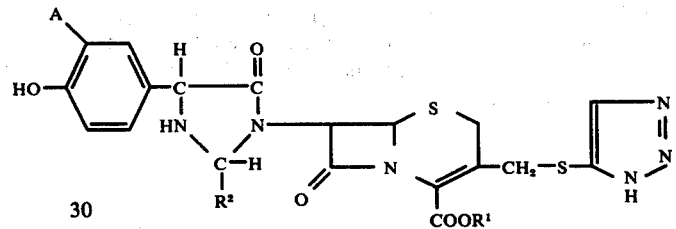

wherein
A is hydrogen, hydroxy, methyl or methoxy,
$R^1$ is hydrogen, sodium or potassium and
$R^2$ is a member selected from the group consisting of 2-furan-5-sulfonic acid, phenyl-2-sulfonic acid, 4-methoxyphenyl-3-sulfonic acid, 4-hydroxyphenyl-3-sulfonic acid, 2-carboxymethoxyphenyl, 4-carboxymethoxyphenyl, 3-hydroxy-4-carboxyphenyl, 4-(2'-carboxy)vinylphenyl, carboxyl, 2-carboxyphenyl, 3-carboxyphenyl, methanesulfonic acid and methanedisulfonic acid in the form of its sodium or potassium salt.

16. A compound of claim 15 wherein $R^2$ is 2-furan-5-sulfonic acid.

17. A compound of claim 15 wherein $R^2$ is phenyl-2-sulfonic acid.

18. A compound of claim 15 wherein $R^2$ is 4-methoxyphenyl-3-sulfonic acid.

19. A compound of claim 15 wherein $R^2$ is 4-hydroxyphenyl-3-sulfonic acid.

20. A compound of claim 15 wherein $R^2$ is 2-carboxymethoxyphenyl.

21. A compound of claim 15 wherein $R^2$ is 4-carboxymethoxyphenyl.

22. A compound of claim 15 wherein $R^2$ is 3-hydroxy-4-carboxyphenyl.

23. A compound of claim 15 wherein $R^2$ is 4-(2'-carboxy)vinylphenyl.

24. A compound of claim 15 wherein $R^2$ is carboxyl.
25. A compound of claim 15 wherein $R^2$ is 2-carboxyphenyl.
26. A compound of claim 15 wherein $R^2$ is 3-carboxyphenyl.
27. A compound of claim 15 wherein $R^2$ is methanesulfonic acid.
28. A compound of claim 15 wherein $R^2$ is methanedisulfonic acid.
29. A compound of the formula

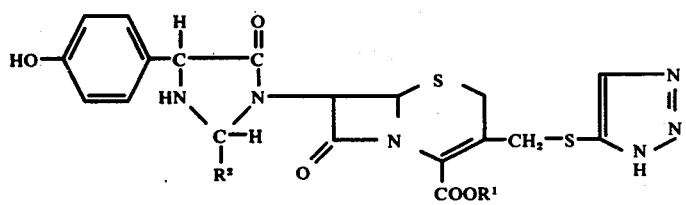

wherein
 $R^1$ is hydrogen, sodium or potassium and
 $R^2$ is a member selected from the group consisting of 2-furan-5 sulfonic acid, phenyl-2-sulfonic acid, 4-methoxyphenyl-3-sulfonic acid, 4-hydroxyphenyl-3-sulfonic acid, 2-carboxymethoxyphenyl, 4-carboxymethoxyphenyl, 3-hydroxy-4-carboxyphenyl, 4-(2'-carboxy)vinylphenyl, carboxyl, 2-carboxyphenyl, 3-carboxyphenyl, methanesulfonic acid and methanedisulfonic acid in the form of its sodium or potassium salt.

30. A compound of claim 29 wherein $R^2$ is 2-furan-5-sulfonic acid.
31. A compound of claim 29 wherein $R^2$ is phenyl-2-sulfonic acid.
32. A compound of claim 29 wherein $R^2$ is 4-methoxyphenyl-3-sulfonic acid.
33. A compound of claim 29 wherein $R^2$ is 4-hydroxyphenyl-3-sulfonic acid.
34. A compound of claim 29 wherein $R^2$ is 2-carboxymethoxyphenyl.
35. A compound of claim 29 wherein $R^2$ is 4-carboxymethoxyphenyl.
36. A compound of claim 29 wherein $R^2$ is 3-hydroxy-4-carboxyphenyl.
37. A compound of claim 29 wherein $R^2$ is 4-(2'-carboxy)vinylphenyl.
38. A compound of claim 29 wherein $R^2$ is carboxyl.
39. A compound of claim 29 wherein $R^2$ is 2-carboxyphenyl.
40. A compound of claim 29 wherein $R^2$ is 3-carboxyphenyl.
41. A compound of claim 29 wherein $R^2$ is methanesulfonic acid.
42. A compound of claim 29 wherein $R^2$ is methanedisulfonic acid.
43. The compound of claim 30 having the D configuration wherein $R^1$ is sodium.
44. The compound of claim 30 having the D configuration wherein $R^1$ is potassium.
45. The compound of claim 30 having the D configuration wherein $R^1$ is hydrogen.
46. A compound of the formula

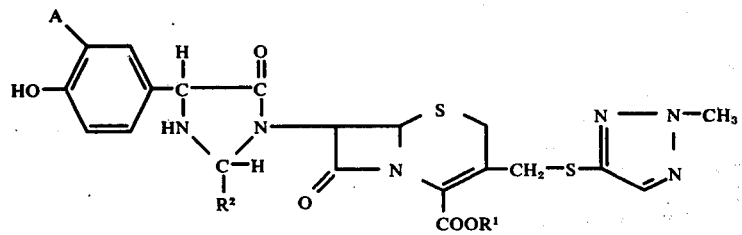

wherein
 A is hydrogen, hydroxy, methyl or methoxy,
 $R^1$ is hydrogen, sodium or potassium and
 $R^2$ is a member selected from the group consisting of 2-furan-5-sulfonic acid, phenyl-2-sulfonic acid, 4-methoxyphenyl-3-sulfonic acid, 4-hydroxyphenyl-3-sulfonicacid, 2-carboxymethoxyphenyl, 4-carboxymethoxyphenyl, 3-hydroxy-4-carboxyphenyl, 4-(2'-carboxy)vinylphenyl, carboxyl, 2-carboxyphenyl, 3-carboxyphenyl, methanesulfonic acid and methanedisulfonic acid in the form of its sodium or potassium salt.

47. A compound of claim 46 wherein $R^2$ is 2-furan-5-sulfonic acid.
48. A compound of claim 46 of the formula

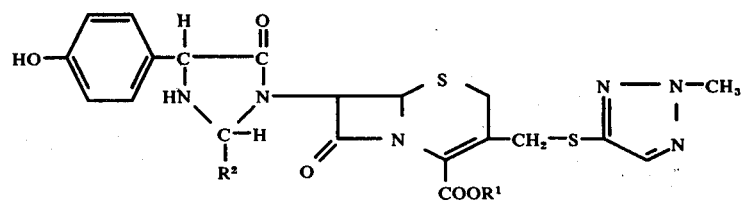

wherein
 $R^1$ is hydrogen, sodium or potassium and
 $R^2$ is a member selected from the group consisting of 2-furan-5-sulfonic acid, phenyl-2-sulfonic acid, 4-methoxyphenyl-3-sulfonic acid, 4-hydroxyphenyl-3-sulfonic acid, 2-carboxymethoxyphenyl, 4- carboxymethoxyphenyl, 3-hydroxy-4-carboxyphenyl, 4-(2'-carboxy)vinylphenyl, carboxyl, 2-carboxyphenyl, 3-carboxyphenyl, methanesulfonic acid and methanedisulfonic acid in the form of its sodium or potassium salt.

49. A compound of claim 48 wherein $R^2$ is 2-furan-5-sulfonic acid.

50. The compound of claim 49 having the D configuration wherein $R^1$ is sodium.

51. The compound of claim 49 having the D configuration wherein $R^1$ is potassium.

52. The compound of claim 49 having the D configuration wherein $R^1$ is hydrogen.

53. A compound of the formula

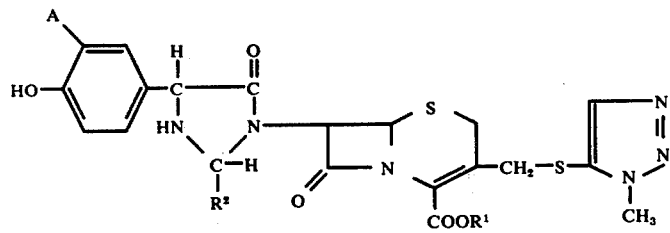

wherein

A is hydrogen, hydroxy, methyl or methoxy,
$R^1$ is hydrogen, sodium or potassium and
$R^2$ is a member selected from the group consisting of 2-furan-5-sulfonic acid, phenyl-2-sulfonic acid, 4-methoxyphenyl-3-sulfonic acid, 4-hydroxyphenyl-3-sulfonic acid, 2-carboxymethoxyphenyl, 4-carboxymethoxyphenyl, 3-hydroxy-4-carboxyphenyl, 4-(2'-carboxy)vinylphenyl, carboxyl, 2-carboxyphenyl, 3-carboxyphenyl, methanesulfonic acid and methanedisulfonic acid in the form of its sodium or potasssium salt.

54. A compound of claim 53 wherein $R^2$ is 2-furan-5-sulfonic acid.

55. A compound of claim 53 of the formula

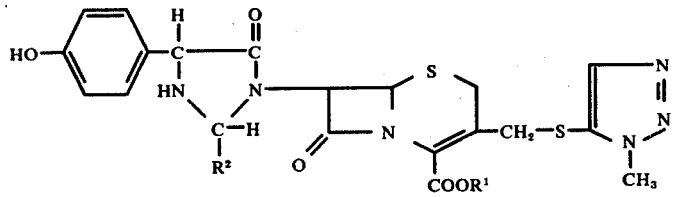

wherein $R^1$ is hydrogen, sodium or potassium and
$R^2$ is a member selected from the group consisting of 2-furan-5-sulfonic acid, phenyl-2-sulfonic acid, 4-methoxyphenyl-3-sulfonic acid, 4-hydroxyphenyl-3-sulfonic acid, 2-carboxymethoxyphenyl, 4-carboxymethoxyphenyl, 3-hydroxy-4-carboxyphenyl, 4-(2'-carboxy)vinylphenyl, carboxyl, 2-carboxyphenyl, 3-carboxyphenyl, methanesulfonic acid and methanedisulfonic acid in the form of its sodium or potassium salt.

56. A compound of claim 55 wherein $R^2$ is 2-furan-5-sulfonic acid.

57. The compound of claim 56 having the D configuration wherein $R^1$ is sodium.

58. The compound of claim 56 having the D configuration wherein $R^1$ is potassium.

59. The compound of claim 56 having the D configuration wherein $R^1$ is hydrogen.

* * * * *